(12) United States Patent
Ruppert et al.

(10) Patent No.: US 10,660,630 B2
(45) Date of Patent: May 26, 2020

(54) RETRACTION DEVICES AND METHODS OF ITS USE AND MANUFACTURE

(71) Applicants: David S. Ruppert, Chapel Hill, NC (US); Alexander G. Verderber, Raleigh, NC (US)

(72) Inventors: David S. Ruppert, Chapel Hill, NC (US); Alexander G. Verderber, Raleigh, NC (US)

( * ) Notice: Subject to any disclaimer, the term of this patent is extended or adjusted under 35 U.S.C. 154(b) by 71 days.

(21) Appl. No.: 15/993,771

(22) Filed: May 31, 2018

(65) Prior Publication Data

US 2018/0338752 A1    Nov. 29, 2018

Related U.S. Application Data

(63) Continuation of application No. 14/604,686, filed on Jan. 24, 2015, now Pat. No. 9,999,414.

(60) Provisional application No. 61/931,218, filed on Jan. 24, 2014.

(51) Int. Cl.
*A61B 17/02* (2006.01)

(52) U.S. Cl.
CPC ................ *A61B 17/0206* (2013.01)

(58) Field of Classification Search
CPC ............................ A61B 17/02; A61B 17/0206
USPC ................................................. 600/201–249
See application file for complete search history.

(56) References Cited

U.S. PATENT DOCUMENTS

| 3,625,586 | A | * | 12/1971 | Olexa | G02B 21/26 359/393 |
| 3,807,393 | A |   | 4/1974  | McDonald | |
| 4,156,424 | A | * | 5/1979  | Burgin | A61B 1/32 600/212 |
| 4,226,228 | A | * | 10/1980 | Shin | A61B 1/32 600/206 |
| 4,421,107 | A |   | 12/1983 | Estes et al. | |
| 4,627,421 | A | * | 12/1986 | Symbas | A61B 17/0206 600/232 |

(Continued)

FOREIGN PATENT DOCUMENTS

| EP | 0792620 A2 | 9/1997 |
| EP | 228014 A1  | 9/2010 |

(Continued)

OTHER PUBLICATIONS

Abrams, Eduard, et. al., Cross-Sectional Geometry of Human Ribs, Biomechanics Laboratory, Legacy Clinical Research & Technology Center, Portland, OR.

(Continued)

*Primary Examiner* — Eric S Gibson
(74) *Attorney, Agent, or Firm* — Olive Law Group, PLLC

(57) ABSTRACT

Rib retraction devices and methods of its use and manufacture are disclosed. A retraction device may include a first frame portion and a second frame portion. The second frame portion may be attached to the first frame portion. The second frame portion may mechanically move between a first position and a second position with respect to the first frame portion. The retraction device may also include a first blade being pivotally attached to the first frame portion and comprising a flexible material. The retraction device may also include a second blade being pivotally attached to the second frame portion and comprising a flexible material.

13 Claims, 18 Drawing Sheets

(56) References Cited

U.S. PATENT DOCUMENTS

| | | | |
|---|---|---|---|
| 4,726,356 A * | 2/1988 | Santilli | A61B 17/0206 600/232 |
| 4,747,394 A * | 5/1988 | Watanabe | A61B 17/0206 600/217 |
| 4,777,943 A | 10/1988 | Chvapil | |
| 4,829,985 A * | 5/1989 | Couetil | A61B 17/0206 600/232 |
| 5,088,472 A * | 2/1992 | Fakhrai | A61B 17/0206 600/214 |
| 5,616,117 A * | 4/1997 | Dinkler | A61B 17/0206 600/210 |
| 5,772,583 A * | 6/1998 | Wright | A61B 17/0206 403/389 |
| 5,779,629 A * | 7/1998 | Hohlen | A61B 17/0293 600/233 |
| 5,865,731 A * | 2/1999 | Lenox | A61B 17/0206 600/232 |
| 5,928,146 A | 7/1999 | Itagaki et al. | |
| 5,931,778 A * | 8/1999 | Furnish | A61B 17/0206 600/232 |
| 5,984,867 A * | 11/1999 | Deckman | A61B 17/0206 600/231 |
| 6,007,552 A | 12/1999 | Fogarty et al. | |
| 6,102,854 A * | 8/2000 | Cartier | A61B 1/32 600/210 |
| 6,113,535 A | 9/2000 | Fox et al. | |
| 6,113,536 A * | 9/2000 | Aboul-Hosn | A61B 17/0206 600/227 |
| 6,159,231 A | 12/2000 | Looney et al. | |
| 6,206,828 B1 * | 3/2001 | Wright | A61B 17/0206 600/232 |
| 6,312,377 B1 * | 11/2001 | Segermark | A61B 17/02 600/201 |
| 6,338,712 B2 * | 1/2002 | Spence | A61B 17/02 600/201 |
| 6,361,492 B1 * | 3/2002 | Santilli | A61B 17/0206 600/205 |
| 6,371,911 B1 | 4/2002 | Hossain et al. | |
| 6,450,983 B1 | 9/2002 | Rambo | |
| 6,500,116 B1 * | 12/2002 | Knapp | A61B 17/0206 600/210 |
| 6,837,851 B1 * | 1/2005 | Valentini | A61B 17/0206 600/210 |
| 7,029,472 B1 * | 4/2006 | Fortin | A61B 17/7014 606/105 |
| 7,056,287 B2 * | 6/2006 | Taylor | A61B 17/00234 600/210 |
| 7,186,215 B2 | 3/2007 | Yi et al. | |
| 7,220,228 B2 * | 5/2007 | Hu | A61B 17/02 600/210 |
| 7,294,103 B2 * | 11/2007 | Bertolero | A61B 17/02 600/201 |
| 7,507,202 B2 * | 3/2009 | Schoellhorn | A61B 17/0206 600/232 |
| 7,537,565 B2 * | 5/2009 | Bass | A61B 17/0206 600/219 |
| 7,850,608 B2 * | 12/2010 | Hamada | A61B 17/0206 600/201 |
| 7,935,054 B2 * | 5/2011 | Hamada | A61B 17/02 600/219 |
| 8,540,628 B2 | 9/2013 | O'Prey et al. | |
| 8,574,155 B2 | 11/2013 | O'Prey et al. | |
| 8,579,806 B2 | 11/2013 | Buckner et al. | |
| 8,758,235 B2 | 6/2014 | Jaworek | |
| 8,777,849 B2 | 7/2014 | Haig et al. | |
| 8,827,902 B2 * | 9/2014 | Dietze, Jr. | A61B 17/0206 600/201 |
| 8,845,527 B2 * | 9/2014 | Crenshaw | A61B 5/0051 600/201 |
| 8,900,137 B1 * | 12/2014 | Lovell | A61B 17/02 600/210 |
| 8,915,845 B2 | 12/2014 | Pell et al. | |
| 9,113,853 B1 * | 8/2015 | Casey | A61B 17/0206 |
| 9,999,414 B2 * | 6/2018 | Ruppert | A61B 17/0206 |
| 2004/0127773 A1 * | 7/2004 | Douglas | A61B 17/02 600/227 |
| 2005/0065429 A1 | 3/2005 | Zhou | |
| 2006/0004261 A1 * | 1/2006 | Douglas | A61B 1/32 600/210 |
| 2006/0084843 A1 * | 4/2006 | Sommerich | A61B 17/02 600/210 |
| 2007/0038216 A1 * | 2/2007 | Hamada | A61B 17/02 606/53 |
| 2007/0083086 A1 * | 4/2007 | LeVahn | A61B 17/02 600/210 |
| 2007/0161865 A1 * | 7/2007 | Fakhrai | A61B 17/0206 600/231 |
| 2007/0219416 A1 * | 9/2007 | Perez-Cruet | A61B 17/02 600/219 |
| 2008/0183046 A1 * | 7/2008 | Boucher | A61B 17/0206 600/232 |
| 2008/0221394 A1 * | 9/2008 | Melkent | A61B 17/0206 600/201 |
| 2009/0076516 A1 * | 3/2009 | Lowry | A61B 17/02 606/90 |
| 2009/0203969 A1 * | 8/2009 | Cohen | A61B 17/02 600/245 |
| 2009/0259107 A1 * | 10/2009 | Crenshaw | A61B 5/0051 600/202 |
| 2009/0259109 A1 | 10/2009 | Bucefari et al. | |
| 2009/0287060 A1 | 11/2009 | Pell et al. | |
| 2010/0022845 A1 | 1/2010 | Ott et al. | |
| 2010/0185081 A1 | 7/2010 | Soher et al. | |
| 2010/0268036 A1 * | 10/2010 | Rothweiler | A61B 17/0206 600/214 |
| 2011/0098537 A1 * | 4/2011 | Justis | A61B 17/0206 600/210 |
| 2011/0172494 A1 * | 7/2011 | Bass | A61B 17/0206 600/215 |
| 2011/0184245 A1 * | 7/2011 | Xia | A61B 17/0206 600/202 |
| 2011/0190588 A1 * | 8/2011 | McKay | A61B 17/0206 600/202 |
| 2011/0208008 A1 | 8/2011 | Michaeli et al. | |
| 2011/0301422 A1 * | 12/2011 | Woolley | A61B 17/0206 600/215 |
| 2012/0022335 A1 * | 1/2012 | Assaker | A61B 17/0206 600/225 |
| 2012/0041272 A1 * | 2/2012 | Dietze, Jr. | A61B 17/0206 600/231 |
| 2012/0130180 A1 * | 5/2012 | Pell | A61B 5/0051 600/206 |
| 2012/0203070 A1 | 8/2012 | Crenshaw et al. | |
| 2012/0265213 A1 * | 10/2012 | Beger | A61B 17/0206 606/102 |
| 2012/0316401 A1 * | 12/2012 | Matsumura | A61B 17/0206 600/235 |
| 2012/0330106 A1 * | 12/2012 | Wright | A61B 17/0206 600/218 |
| 2013/0225936 A1 * | 8/2013 | Alexander | A61B 1/303 600/235 |
| 2013/0237766 A1 * | 9/2013 | Pell | A61B 7/00 600/211 |
| 2013/0237769 A1 * | 9/2013 | Puskas | A61B 1/32 600/232 |
| 2014/0005484 A1 * | 1/2014 | Charles | A61B 17/02 600/201 |
| 2015/0018624 A1 * | 1/2015 | Beck | A61B 1/32 600/206 |
| 2015/0209022 A1 * | 7/2015 | Ruppert | A61B 17/0206 600/219 |
| 2016/0000419 A1 * | 1/2016 | Weisshaupt | A61B 17/0206 600/225 |
| 2016/0213365 A1 * | 7/2016 | Vogtherr | A61B 17/0206 |

(56) References Cited

U.S. PATENT DOCUMENTS

2016/0242757 A1* 8/2016 Cryder ............... A61B 17/0206
2016/0287224 A1* 10/2016 Castro .................... A61B 13/00

FOREIGN PATENT DOCUMENTS

| EP | 2462883 A1 | 6/2012 |
|---|---|---|
| JP | 2009279390 A | 12/2009 |
| WO | 2006012535 A1 | 2/2006 |
| WO | 2009140495 A2 | 11/2009 |
| WO | 2013036921 A1 | 3/2013 |

OTHER PUBLICATIONS

Aigner, Philipp, et al., Sternal force distribution during median sternotomy retraction, The Journal of Thoracic and Cardiovascular Surgery, 2013, The American Association for Thoracic Surgery.

Ailawadi, Gorav, MD., et. al., The Legends Behind Cardiothoracic Surgical Instruments, Ann Thorac, 2010, pp. 1693-1700, vol. 89, The Society of Thoracic Surgeons by Elsevier Inc., Charlottesville, VA.

Arora, Dheeraj, et al., Fracture of first rib after sternotomy, Indian Journal of Anaesthesia, Mar.-Apr. 2011, 212-214, vol. 55, Indian Journal of Anaesthesia.

Bayman, Emine O., et al., Incidence and Severity of Chronic Pain at 3 and 6 Months After Thoracotomy: Meta-Analyses, Journal of Pain, 2014.

Bayram, Ahmet S., et al., Rib approximation without intercostal nerve compression reduces post-thoracotomy pain: a prospective randomized study, European Journal of Cardio-Thoracic Surgery, 2011, pp. 570-574, vol. 39, Elsevier, B.V., Bursa, Turkey.

Boaron, Maurizio, A New Retraction-Suspension Device for Limited Upper Sternotomy, Ann Thorac Surg, The Society of Thoracic Surgeons, 2004, pp. 1107-1108, vol. 77,Elsevier, Inc., Bologna, Italy.

Bolotin, Gil, et al., A novel instrumented retractor to monitor tissue-disruptive forces during lateral thoracotomy, The Journal of Thoracic and Cardiovascular Surgery, Apr. 2007, 949-954, vol. 133, No. 4, The American Association for Thoracic Surgery.

Bolotin, Gil, et al., Tissue-Disruptive Forces during Median Sternotomy, The Heart Surgery Form #2007-1121, Dec. 2007, Forum Multimedia Publishing, LLC.

Bonfils-Roberts, E.A., MD, The Rib Spreader: A Chapter in the History of Thoracic Surgery, Chest, May 1972, pp. 469-474 , vol. 61, No. 5, Department of Surgery, St. Vincent's Hospital and Medical Center of New York City, New York.

Byrd, Richard, et al., Cough Dynamics in the Post-Thoracotomy State, Jun. 6, 1975.

Cerfolio, Robert J. et al., Intracostal Sutures Decrease the Pain of Thoracotomy, Ann Thorac Surg, The Society of Thoracic Surgeons, 2003, pp. 407-412, vol. 76, Elsevier, Inc., Birmingham, AL.

Cerfolio, Robert J., et al., A Nondivided Intercostal Muscle Flap Further Reduces Pain of Thoracotomy: A Prospective Randomized Trial, Ann Thorac Surg, The Society of Thoracic Surgeons, 2008, pp. 1901-1907, vol. 85, Elsevier, Inc., Birmingham & Mobile, AL.

Cerfolio, Robert J., Intercostal muscle flap reduces the pain of thoracotomy: A prospective randomized trial, The Journal of Thoracic and Cardiovascular Surgery, 2005, pp. 987-993, vol. 130, No. 4, American Association for Thoracic Surgery, Birmingham, AL.

Chang, Pei Yeh, et. al., Preliminary analysis of the forces on the thoracic cage of patients with pectus excavatum after the Nuss procedure, 2008, pp. 881-885, vol. 23, Elsevier, Taiwan.

Chaux, Aurelio, et al., A New Concept in Sternal Retraction: Applications for Internal Mammary Artery Dissection and Valve Replacement Surgery, The Annals of Thoracic Surgery, Oct. 1986, pp. 473-474, vol. 42, No. 4, Department of Thoracic and Cardiovascular Surgery, Los Angeles, CA.

Cheng, Lei, et al., Evaluation of liver tissue damage and grasp stability using finite element analysis, Computer Methods in Biomechanics and Biomedical Engineering, 2014, Taylor & Francis Group, Seattle, WA.

Chong, A Y, et al., Brachial plexus injury as an unusual complication of coronary artery bypass graft surgery, Postgrad Med J, 2003, 84-86, vol. 79.

De la Fuente, Sebastian G. Enrique Finochietto: The Legacy of Surgery in Argentina, Journal of Surgical Education, Mar./Apr. 2007, pp. 120-123, vol. 64, No. 2, Association of Program Directors in Surgery Published by Elsevier Inc., Durham, NC.

Delrossi, A.J., et al., A New Retractor to Aid in Coronary Artery Surgery, The Annals of Thoracic Surgery, Jul. 1983, pp. 101-102, vol. 36, No. 1, The Department of Thoracic and Cardiovascular Surgery, Browns Mills, NJ.

Dixon, D.S., et al., Rib Spreader Laceration: A Confusing Artifact of Emergency Thoracotomy, Journal of Forensic Sciences, Jan. 1983, 255-262, vol. 28, No. 1, ASTM International.

Dones, Ainhitze, Finite Element Simulation: Tensile test of rib cortical bone, Master's Thesis, 2010:04, Department of Applied Mechanics, Division of Vehicle Safety, Chalmers University of Technology, Goteborg, Sweden.

Espinoza, Andreas, et al., Wide sternal retraction may impede internal mammary artery graft flow and reduce myocardial function during off-pump coronary artery bypass grafting: presentation of two cases, Interactive CardioVascular and Thoracic Surgery, 2012, 42-44, vol. 15, Oxford University.

Forman, Jason L., et. al., Predicting Rib Fracture Risk With Whole-Body Finite Element Models: Development and Preliminary Evaluation of a Probabilistic Analytical Framework, Annals of Advances in Automotive Medicine, Oct. 14-17, 2012, pp. 109-124, vol. 56, 56th AAAM Annual Conference Annals of Advances in Automotive Medicine, Charlottesville, VA.

Freynet, Anne, et. al., Is transcutaneous electrical nerve stimulation effective in relieving postoperative pain after thoracotomy?, Interactive Cardiovascular and Thoracic Surgery, 2010, pp. 283-288, vol. 10, European Association for Cardio-Thoracic Surgery, France.

Gerner, Peter, MD., Post-thoracotomy Pain Management Problems, Anesthesiol Clin., Jun. 2008, pp. 1-12, NIH-PA Author Manuscript, Boston, MA.

Gonzalez, Luis Berlanga, et. al., Chest Wall Paraesthesia After Thoracic Surgery, Paresthesia, Feb. 2012, pp. 17-33, InTech, Caceres, Spain.

Gordy, Stephanie, MD, et. al., The contribution of rib fractures to chronic pain and disability, The American Journal of Surgery, 2014, pp. 659-663, vol. 207, No. 5, Elsevier, Inc., Portland, OR.

Gottschalk, Allan, MD,PhD, et. al., Clinical and Demographic Characteristics of Patients With Chronic Pain After Major Thoracotomy, Clin J Pain, Oct. 2008, pp. 708-716, vol. 24, No. 8, Lippincott Williams & Wilkins, Baltimore, MD.

Grocott, Hilary P., et. al., "Other" Neurologic Complications After Cardiac Surgery, Seminars in Cardiothoracic and Vascular Anesthesia, Sep. 2004, pp. 212-226, vol. 8, No. 3, Sage Publications.

Grosen, Kasper, et. al., Perioperative gabapentin for the prevention of persistent pain after thoracotomy: a randomized controlled trial, European Journal of Cardio-Thoracic Surgery, Feb. 28, 2014, pp. 1-10, Oxford University Press on behalf of the European Association for Cardio-Thoracic Surgery, UK.

Guastella, Virginie, et. al., A prospective study of neuropathic pain induced by thoracotomy: Incidence, clinical description, and diagnosis, Pain, 2011, pp. 74-81, vol. 152, Elsevier, France.

Healey, Scott, et. al., Does retraction of the sternum during median sternotomy result in brachial plexus injuries?, Interactive CardioVascular and Thoracic Surgery, Mar. 19, 2013, pp. 151-157, vol. 17, Oxford University Press on behalf of the European Association for Cardio-Thoracic Surgery, UK.

Mohite, Prashant, N. et al., Utilization of a Novel Rib Spreader for Minimally Invasive Lung Transplantation, Surgical Innovation, 2014, pp. 1-2, Sage Publications, London, UK.

Hughes, Richard, et. al., Pain control for thoracotomy, Continuing Education in Anaesthesia, Critical Care & Pain, 2005, pp. 56-60, vol. 5, No. 2, The Board of Management and Trustees of the British Journal of Anaesthesia, Birmingham.

(56) References Cited

OTHER PUBLICATIONS

Hunt, Ian, et al., Reducing post-thoracotomy wound pain by limited mobilisation of the intercostal muscle neurovascular bundle prior to wound retraction, Ann R Coll Surg Engl, 2008, pp. 616-617, vol. 90, Ann R Coll Surg Engl, Middlesex, UK.
Jarit—Rib Spreaders-Retractors, Thoracic and Cardiovascular.
Jellish, W. Scott, et al., Somatosensory Evoked Potential Monitoring Used to Compare the Effect of Three Asymmetric Sternal Retractors on Brachial Plexus Function, Anesth Analg, 1999, Departments of Anesthesiology and Thoracic and Cardiovascular Surgery, Loyola University Medical Center, Maywood, IL.
Kehlet, Henrik, et. al., Persistent postsurgical pain: risk factors and prevention, Review, May 2006, pp. 1618-1625, vol. 367, Lancet.
Kemper, Andrew R., et. al., The Biomechanics of Human Ribs: Material and Structural Properties from Dynamic Tension and Bending Tests, Stapp Car Crash Journal, Oct. 2007, pp. 235-273, vol. 51, The Strapp Association, Blacksburg, VA.
Khelemsky, Yury, MD, et. al., Preventing Post-Thoracotomy Pain Syndrome, Mount Sinai Journal of Medicine, 2012, pp. 133-139, vol. 79, Department of Anesthesiology, Mount Sinai School of Medicine, New York, NY.
Kieser, Jules A., et. al., Compressive rib fracture: Peri-mortem and post-mortem trauma patterns in a pig model, Legal Medicine, 2013, pp. 193-201, vol. 15, Elsevier, New Zealand.
Kirkup, John R., The history and evolution of surgical instruments: XI Retractors, dilators and related inset pivoting instruments, Ann R Coll Surg Engl, 2002, pp. 149-155, vol. 84, Royal College of Surgeons of England, London, UK.
Kofidis, Theo, et al., A Novel and Simple Atrial Retractor, Ann Thorac Surg, The Society of Thoracic Surgeons, 2011, pp. 1634-1635, vol. 91, Elsevier, Inc., Singapore.
Koop, Olga, et al., The role of intercostal nerve perservation in pain control after thoracotomy, European Journal of Cardio-Thoracic Surgery Advance Access, Aug. 24, 2012, Oxford University Press.
Kotkar, Kunal D., et al., Reduced left internal mammary artery blood flow on normal sternal retraction, Asian Cardiovascular & Thoracic Annals, , 2013, Sage Publications, Mohali, India.
Marchetti-Filho, Marco A., The role of intercostal nerve preservation in acute pain control after thoracotomy, J Bras Pneumol, 2014, pp. 164-170, vol. 40(2), J Bras Pneumol, Sao Paulo, Brazil.
McConaghie, F.A., et al., The role of retraction in direct nerve injury in total hip replacement, Bone and Joint Research, Jun. 2014, 212-216, vol. 3, No. 6, The British Editorial Society of Bone & Joint Surgery.
Miyazaki, Takuro, et al., Assessment and follow-up of intercostal nerve damage after video-assisted thoracic surgery, European Journal of Cardio-Thoracic Surgery, 2011, 1033-1039, vol. 39, Elsevier B.V., Nagasaki, Japan.
Yasuda, Tamotsu, et al., A Novel Figure A-Shape Sternal Retractor for Off-Pump Coronary Artery Bypass Grafting, The Heart Surgery Forum, 2005, pp. E196-E197, Forum Multimedia Publishing, LLC, Kanazawa, Ishikawa, Japan.
Mohr, Marcus, et. al., Geometry of human ribs pertinent to orthopedic chest-wall reconstruction, Journal of Biomechanics, 2007, pp. 1310-1317, vol. 40, Elsevier, Ltd., Portland, OR.
Moore, Robert, MD, et. al, Poststernotomy Fractures and Pain Management in Open Cardiac Surgery, Chest, Nov. 1994, pp. 1339-1342, vol. 106, No. 5, Division of Cardiothoracic Surgery, Univesity of California, Davis, Medical Center, Sacramento, CA.
Navarro Thoracic Retractor, Pierson Surgical Ltd., www.piersonsurgical.com.
Onwere, Joyce L., et al., Intraoperative Hypoxemia from Compression of the Right Pulmonary Artery Caused by a Sternal Retractor, Anesthesia & Analgesia, Feb. 2008, 415-416, vol. 106, No. 2, International Anesthesia Research Society.
Pailler-Mattei, C. et. al., In vivo measurements of the elastic mechanical properties of human skin by indentation tests, Medical Engineering & Physics, 2008, pp. 599-606, vol. 30, Elsevier, France.

PCT International Search Report and Written Opinion for PCT/US2012/065134 dated Feb. 19, 2013.
PCT Search Report and Written Opinion dated May 13, 2015 for PCT Application PCT/US2015/012793.
Perttunen, K., et. al., Chronic pain after thoracic surgery: a follow-up study, Ada Anaesthesiol Scandinavica, 1999, pp. 563-567, vol. 43, Acta Anaesthesiol Scandinavica, Helsinki, Finland.
Perz, Rafal, et. al., Variation in the human ribs geometrical properties and mechanical response based on X-ray computed tomography images resolution, Journal of the Mechanical Behavior of Biomedical Materials, 2015, pp. 292-301, vol. 41, Elsevier, Warsaw Poland & Charlottesville, VA.
Rogers, M.L., et al., Preliminary findings in the neurophysiological assessment of intercostal nerve injury during thoracotomy, European Journal of Cardio-Thoracic Surgery, 2002, 298-30, vol. 21, Elsevier, Nottingham, UK.
Rogers, Mark L., et al., Surgical aspects of chronic post-thoracotomy pain, European Journal of Cardio-Thoracic Surgery, Sep. 5, 2000, 711-716, vol. 18, Elsevier Science B.V., Nottingham, UK.
Rollins, Josh, et. al., Emergency Cardiac Anterolateral Thoracotomy Simulator, Fall 2009, pp. 1-163, University of Michigan Hospital.
Romero, MD, et. al., The State of the Art in Preventing Post-thoracotomy Pain, Seminars in Thoracic and Cardiovascular Surgery, 2013, pp. 116-124, vol. 25, No. 2, Elsevier.
Sakakura, Noriaki, et al., Assessment of Long-Term Postoperative Pain in Open Thoracotomy Patients: Pain Reduction by the Edge Closure Technique, Ann Thorac Surg, The Society of Thoracic Surgeons, 2010, pp. 1064-1070, vol. 89, Elsevier, Inc., Nagoya, Japan.
Shanghai Retractors, Millennium Surgical Corp., Narberth, PA, millenniumsurgical.com.
Sharma, Ajeet D., MD, et. al., Peripheral Nerve Injuries During Cardiac Surgery: Risk Factors, Diagnosis, Prognosis, and Prevention, Anesthesia & Analgesia, Department of Anesthesiology, Duke University Medical Center, Durham, NC.
Strebel, Bruno M., et al., What's your call?, Clinical Vistas Briefs, Oct. 23, 2007, 1027& 1029, vol. 177(9), Canadian Medical Association.
TeDan Surgical Innovations, www.tedansurgical.com.
Tirado, Javier G., et al., Suture Techniques of the Intercostal Space in Thoracotomy and Their Relationship With Post-Thoracotomy Pain: A Systematic Review, Archivos De Bronconeumologia, 2012, pp. 22-28, vol. 48(1), Elsevier Espana, S.L., Zaragoza, Spain.
Ultravision CT Minimally Invasive Retractor, TeDan Surgical Innovations, LLC, Houston, Texas.
Visagan, Ravindran, et al., Are intracostal sutures better than pericostal sutures for closing a thoracotomy?, Interactive Cardiovascular and Thoracic Surgery, 2012, pp. 807-815, vol. 14, Oxford University Press, European Association for Cardio-Thoracic Surgery, London, UK.
Wexler Retractors, Millennium Surgical Corp., Narberth, PA, millenniumsurgical.com.
Williams, Eric H., et. al., Neurectomy for Treatment of Intercostal Neuralgia, Ann Thorac Sur, 2008, pp. 1766-1770, vol. 85, The Society of Thoracic Surgeons, Elsevier, Inc. Baltimore, MD.
Woodring, John H., et al., Upper Rib Fractures Following Median Sternotomy, The Annals of Thoracic Surgery, Apr. 1985, vol. 39 No. 4, Departments of Diagnostic Radiology and Cardiovascular and Thoracic Surgery, Albert B. Chandler Medical Center,University of Kentucky, Lexington, KY.
Wu, Nan, et al., A prospective, single-blind randomised study on the effect of intercostal nerve protection on early post-thoracotomy pain relief, European Journal of Cardio-thoracic Surgery, 2010, pp. 840-845, vol. 37, Elsevier B.V., Beijing, China.
Restriction Requirement issued in counterpart U.S. Appl. No. 14/604,686 dated Aug. 16, 2017.
Non-Final Office Action issued in counterpart U.S. Appl. No. 14/604,686 dated Oct. 20, 2017.
Notice of Allowance issued in counterpart U.S. Appl. No. 14/604,686 dated Feb. 22, 2018.

(56) References Cited

OTHER PUBLICATIONS

International Preliminary Report on Patentability and Written Opinion issued in PCT Application No. PCT/US2015/012793 dated Jul. 26, 2016 (ten (10) pages).

\* cited by examiner

RETRACTION DEVICES AND METHODS OF ITS USE AND MANUFACTURE

CROSS REFERENCE TO RELATED APPLICATION

This application claims priority to and the benefit of U.S. patent application Ser. No. 14/604,686, filed Jan. 24, 2015, and titled RETRACTION DEVICES AND METHODS OF ITS USE AND MANUFACTURE, which claims priority to and the benefit of U.S. Provisional Patent Application No. 61/931,218, filed Jan. 24, 2014 and titled RIB RETRACTOR; the disclosures of which are incorporated herein by reference in their entireties.

TECHNICAL FIELD

The presently disclosed subject matter relates to medical device systems and methods of making and using the systems. Particularly, the present subject matter relates to retraction devices for separating ribs for thoracic surgeries, as well as methods of making and using the retraction devices.

BACKGROUND

For treating a medical condition, such as a diseased tissue present in an esophageal or spinal tumor, a failing heart valve, or cancerous lungs, surgeons may need to gain direct access to a thoracic cavity of a patient to perform surgery. Typically, surgeons gain access by performing open-chest procedures where the patient's sternum is split and separated for organ exposure. While this technique has provided surgeons with sufficient visualization of target organs in the thorax, it is extremely invasive and can cause the patient to suffer through a painful and prolonged post-surgical recovery.

There exist some minimally invasive techniques for thoracic access that are less disruptive to a patient's body. Thoracotomy procedure is one of the minimally invasive techniques that is widely performed on hundreds of thousands of people each year worldwide. In a thoracotomy procedure, the surgeon gains access to the inner thoracic cavity by physically separating the patient's ribs to create an opening into the thorax through which tools and video scopes can be passed through during the surgery. To perform the thoracotomy procedure, the surgeon may make a lateral skin incision on the patient's torso to expose the underlying chest wall. Subsequently, the surgeon may laterally cut the intercostal muscle or remove it from one of the ribs to create a space between the ribs that can be opened physically with a thoracic retraction device. Once the retraction device is installed in the incision, the surgeon can manually open the space using the hand-operated retraction device. The most common opening mechanism includes a Finochietto rack-and-pinion gear system that retracts the blades a fixed incremental distance per handle turn.

These retractors, which are also used for sternotomies have been successful in creating visual access for the surgeons but have always been the primary source for significant pain and complications that nearly half of all thoracotomy patients experience for months after their procedures. A neurovascular bundle in humans and large mammals runs along the bottom edge of each rib. Disturbance and damage to the intercostal nerve is nearly inevitable in every thoracotomy procedure and physical compression of the intercostal nerve by retractors is the leading cause of patients to experience painful breathing for a significant period of time after the surgery.

The tissue engaging structures, referred to as blades, for typical thoracic retraction devices (or retractors) are typically constructed of surgical grade stainless steel. The blades of these retractor usually have a flat planar surface, which can be continuous or fenestrated. When the flat blades press against the intercostal tissue during retraction, high concentrations of mechanical stress occur at the distal ends of the metal blade. At these distal ends of the blade, the tissue pivots and bends over the middle surface of the blade. The concentration of stress at the distal ends of the blades can be so great that not only does the intercostal nerve get crushed at these local points, but the patient may experience one or more rib fracturing at these same points. The negative consequences of this problem are not only felt by the patients. The significant nerve damage and rib fractures that the patients experience can be detrimental to the cost-saving interests of the hospitals during the acute phase of the cycle of care for the patients.

In view of the foregoing, there is a need for improved retraction devices and methods.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Disclosed herein are the embodiments of a retraction device that may include retractor blades. The retraction device may be designed to engage patient tissue with a flexible material that may minimize maximum forces exerted on the patients' tissues and bones by increasing the contact surface area between the retractor blades and tissue, independent of the patient's unique anatomical intercostal features. The minimization of local stresses applied to the patient's tissues during thoracic retraction in turn may reduce surgical damage to the patient's intercostal and inter-sternal tissue. A flexible blade may be pressed against intercostal tissue and the blade may change shape to match a radius of curvature of the tissue that is being displaced. The retraction device may further be designed with an area moment of inertia and modulus of elasticity in mind to account for the engagement of more than one type of tissue in a single instance.

An embodiment of the present disclosure provides a retraction device having a first frame portion and a second frame portion. The second frame portion may be attached to the first frame portion. The second frame portion may mechanically move between a first position and a second position with respect to the first frame portion. The retraction device may also include a first blade being pivotally attached to the first frame portion and may include a flexible material. The retraction device may also include a second blade being pivotally attached to the second frame portion and may include a flexible material.

Another embodiment of the present disclosure provides a retraction device including a first frame portion including a proximal end and a distal end. The first frame portion may define a number of teeth extending between the proximal end and the distal end. The retraction device may also include a second frame portion being attached to and mechanically movable between a first position and a second position with respect to the first frame portion. The retraction device may also include a first blade pivotally attached to the first frame portion. The first blade may include a flexible material. The retraction device may further include a second blade pivotally attached to the second frame portion. The second blade may include a flexible material. The retraction device may further include a lever and gear mechanism attached to the second frame portion. The lever and gear mechanism may be configured to engage the teeth for moving the second frame portion between the first position and the second position. The retraction device may also include a multiple drive system operably engaged with the lever and gear mechanism. The multiple drive system may be configured to control the lever and gear mechanism in at least two different speeds for displacement rates per full rotation of the lever.

A further embodiment of the present disclosure provides a retraction device including a first frame portion and a second frame portion being attached to the first frame portion. The second frame portion is mechanically movable between a first position and a second position with respect to the first frame portion. The retraction device may also include a first blade being pivotally attached to the first frame portion and defining a surface having a locking structure. The retraction device may also include a second blade being pivotally attached to the second frame portion and defining a surface having a locking structure. The surfaces of the first and second blade may face each other. The locking structures can interlock with one another to prevent pivoting of the first blade and second blade when the surfaces are brought into proximity with one another.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1A:
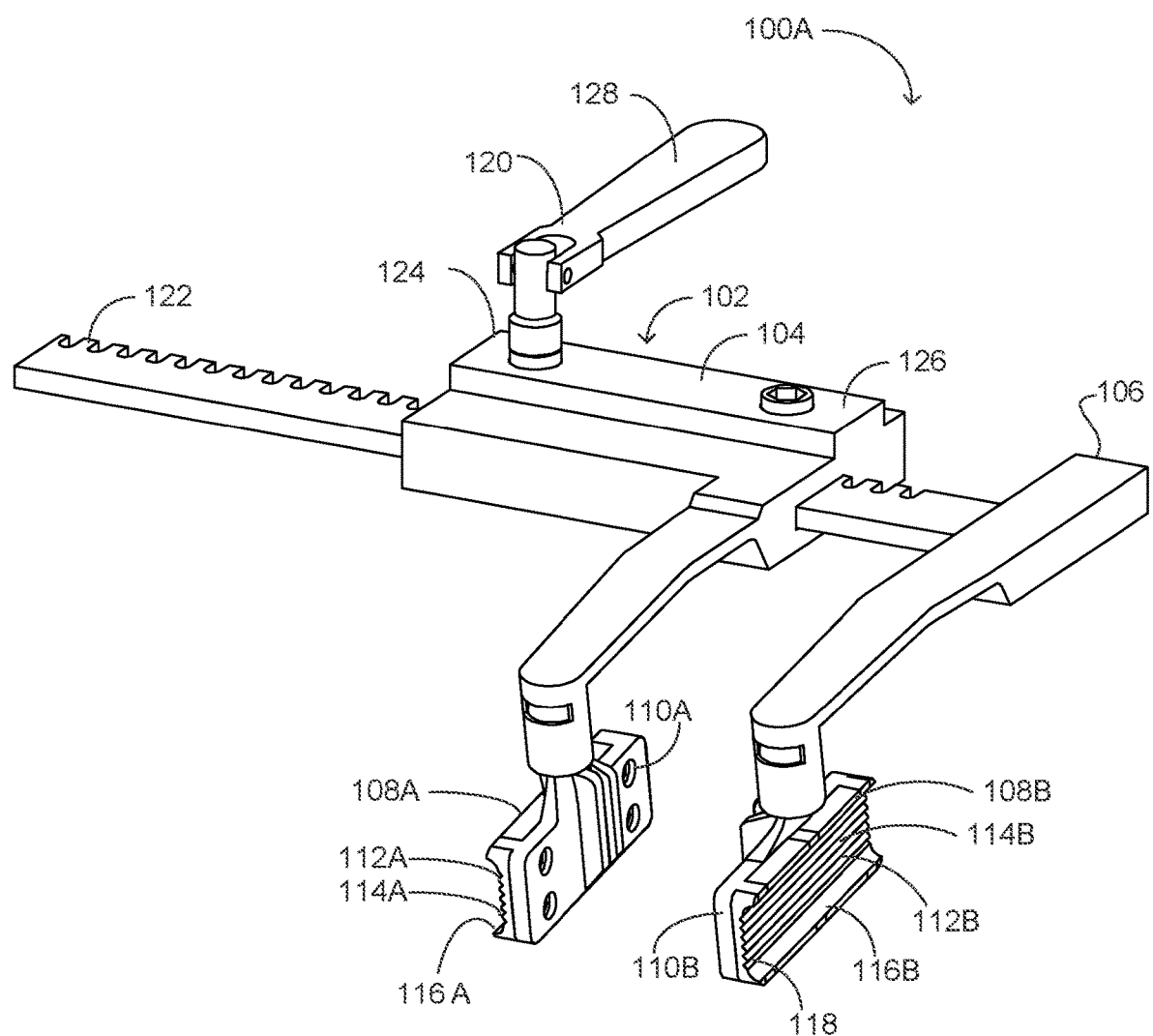
FIG. 1A is a perspective view of an exemplary retraction device according to an embodiment of the present disclosure.

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Reference throughout this specification to "a select embodiment," "one embodiment," or "an embodiment" means that a particular feature, structure, or characteristic described in connection with the embodiment is included in at least one embodiment of the disclosed subject matter. Thus, appearances of the phrases "a select embodiment," "in one embodiment," or "in an embodiment" in various places throughout this specification are not necessarily referring to the same embodiment.

Furthermore, the described features, structures, or characteristics may be combined in any suitable manner in one or more embodiments. In the following description, numerous specific details are provided, to provide a thorough understanding of embodiments of the disclosed subject matter. One skilled in the relevant art will recognize, however, that the disclosed subject matter can be practiced without one or more of the specific details, or with other methods, components, materials, etc. In other instances, well-known structures, materials, or operations are not shown or described in detail to avoid obscuring aspects of the disclosed subject matter.

All numeric values are herein assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings, in which similar elements in different drawings are identified with the same reference numbers. The drawings, which are not necessarily to scale, depict illustrative embodiments and are not intended to limit the scope of the disclosure.

Embodiments of the present disclosure provides a rib retraction device or rib retractor that may be designed to engage patient's tissue in a way that minimizes maximum pressure exerted on the patients' tissues and bones by increasing a contact surface area between retractor blades and the tissue. The minimization of maximum pressure applied to the patient's tissues during thoracic retraction may in turn reduce surgical damage to the patient's intercostal and intrasternal tissue. Damage to the intercostal nerve bundle and rib fractures are major contributors to post-surgical chronic pain that many patients experience after thoracotomies. Many of the rib fractures that occur are due to application of highly concentrated pressure points on the distal edges of the currently used stainless steel retractor blades.

The minimization of maximum forces exerted on the patient's tissue may be achieved by distributing the applied force to the patient's body in the lateral direction by increasing the contact surface area between the retractor blade and tissue. The distribution of the applied forces between the patient's tissue and the retractor blade contact surfaces prevents highly concentrated forces from being applied to the patient's body.

FIG. 1A is a perspective view 100A of an exemplary retraction device 102 according to an embodiment of the present disclosure. The retraction device 102 may include a first frame portion 104 and a second frame portion 106. The first frame portion 104 may also include a proximal end 124 and a distal end 126. The first frame portion 104 may define multiple teeth 122 extending between the proximal end 124 and the distal end 126. Further, the second frame portion 106 may be attached to the first frame portion 104. The second frame portion 106 may be configured to move between a first position and a second position with respect to the first frame portion 104. FIG. 1A shows the retraction device 102 where the second frame portion is in the first position. Further, the first frame portion 104 and the second frame portion 106 may be formed using a rigid material such as, but not limited to, medical grade stainless steels, biocompatible polymer plastics, rigid fiber composites, and the like. In some embodiments, the first frame portion 104 and the second frame portion 106 includes sterilizable material.

The retraction device 102 may further include a first blade 108A attached to the first frame portion 104. The first blade 108A may include a flexible material, which may allow flexible movement of the first blade 108A. The retraction device 102 may also include a second blade 108B pivotally attached to the second frame portion 106. The second blade 108B may include a flexible material, which may allow flexible movement of the second blade 108B. In some embodiments, the rigid material of the first frame portion 104 and the second frame portion 106 may have a flexural stiffness that resists deformation under normal retraction forces. The frame portions 104 and 106 may be made of stainless steel or another material with having a modulus of elasticity of about 190 GPa. Further, the first blade 108A and the second blade 108B may be configured to apply spreading forces on the ribs or one or more tissues of a patient. In some embodiments, the first blade 108A and the second blade 108B are configured to apply spreading forces between a range of 0 and 300 pounds.

In further embodiments, each of the first blade 108A and the second blade 108B may include a flexible component. The flexible component of the first blade 108A may be pivotally attached to the first frame portion 104. Similarly, the flexible component of the second blade 108B may be pivotally attached to the second frame portion 106. The flexible component of the first blade 108A may have a first surface 110A and a second surface 112A. Similarly, the flexible component of the second blade 108B may have a first surface 110B and a second surface 112B. The first surfaces 110A-110B may substantially oppose the second surfaces 112A-112B, respectively. The first surface 110A of the first flexible component of the first blade 108A may face the first surface 110B of the second flexible component of the second blade 108B. Further, each of the first surfaces 110A-110B may include a locking structure. The locking structures may interlock with one another to prevent pivoting of the first blade 108A and the second blade 108B when the first surfaces 110A-110B are brought into proximity with one another. The locking structures may be in the form of a pin or tab, which can be manually toggled or actuated to permit rotational movement. In some embodiments, the locking structure can be provided on one or both of the blades 108A-108B.

Further, the first blade 108A may include a padding material 114A attached to the second surface 112A of the first blade 108A. Similarly, the second blade 108B may include a padding material 114B attached to the second surface 112B of the second blade 108B.

In some embodiments, the first blade 108A is removably attached to the first frame portion 104, and the second blade 108B is removably attached to the second frame portion 106. In an example, the thickness of the blade may be between just over 0 mm and 10 mm, or between about 2 mm and about 4 mm. In an example, the length of a blade may be between about 55 mm and about 65 mm and the width of the blade may be between 25 mm and 35 mm.

Each of the first blade 108A and the second blade 108B may define at least one edge 116A-116B, respectively. Each of the edges 116A-116B may include ridges, such as ridges 118 on the edge 116B, for gripping the one or more tissues. The ridges (such as ridges 118) are segmented along a length of the at least one edge 116A-116B for allowing flexure of the respective first blade 108A or the second blade 108B. In some embodiments, the first blade 108A and the second blade 108B are rotatable.

The padding materials 114A-114B of blades 108A-108B can allow for conforming to small irregularities in the rib bone. The edges 116A-116B may be curved edges. Each of the edges 116A-116B may include a silicone lip curvature to help to stabilize the retraction device 102 in the patient's body along the z-axis. This may help the first and second blades 108A-108B to stay in position between the ribs or sternum.

As shown, the retraction device 102 may also include a lever and gear mechanism 120 (or a gear device 120) attached to the second frame portion 106. The lever and gear mechanism 120 may be configured to engage the teeth 122 for moving the second frame portion 106 between the first position and the second position.

In some embodiments, a multiple gear mechanism is provided described in detail with reference to FIGS. 10-11. For example, the retraction device 102 can include a variable number of gears per unit length of the frame portions 104-106 to generate a more gradual opening of the chest per turn of the opening mechanism. This can be accomplished by having smaller gaps between the teeth 122 as the first frame portion 104 moves along the length of the retraction device 102. The multiple gear mechanism may be able to provide retraction speeds from 0 to 20 mm per handle rotation. Other example speeds are about 7.5 mm and about 15 mm per handle rotation.

In the embodiment, the handle 128 is provided on the retraction device 102 for allowing the surgeon to adjust down the rate at which the tissue is separated by pushing or pulling the handle and changing the diameter of the gear that moves down the frame portions 104-106. This can be accomplished by having a first conical gear structure, connected to a second conical gear structure by a fixed belt. When the handle 128 is pushed, the first conical gear structure slides on a shaft, thus changing the gear ratio through the belt to the second conical gear element. By increasing or decreasing the number of gears per unit length of the retractor frame or the gear ratio, the surgeon can slowly or quickly open up the thorax and avoid fracturing ribs.

Figure 6:
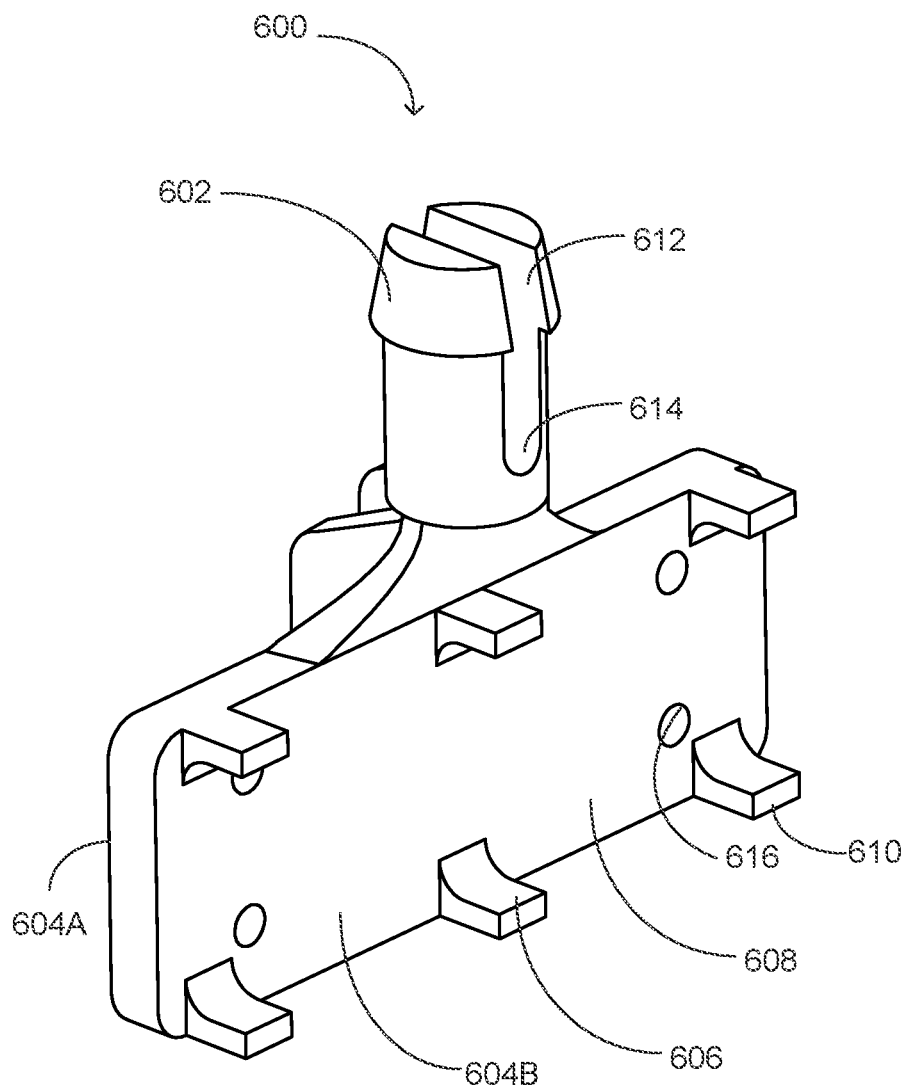
FIG. 6 is a perspective view of an exemplary blade of a retraction device according to an embodiment of the present disclosure.
Figure 7:
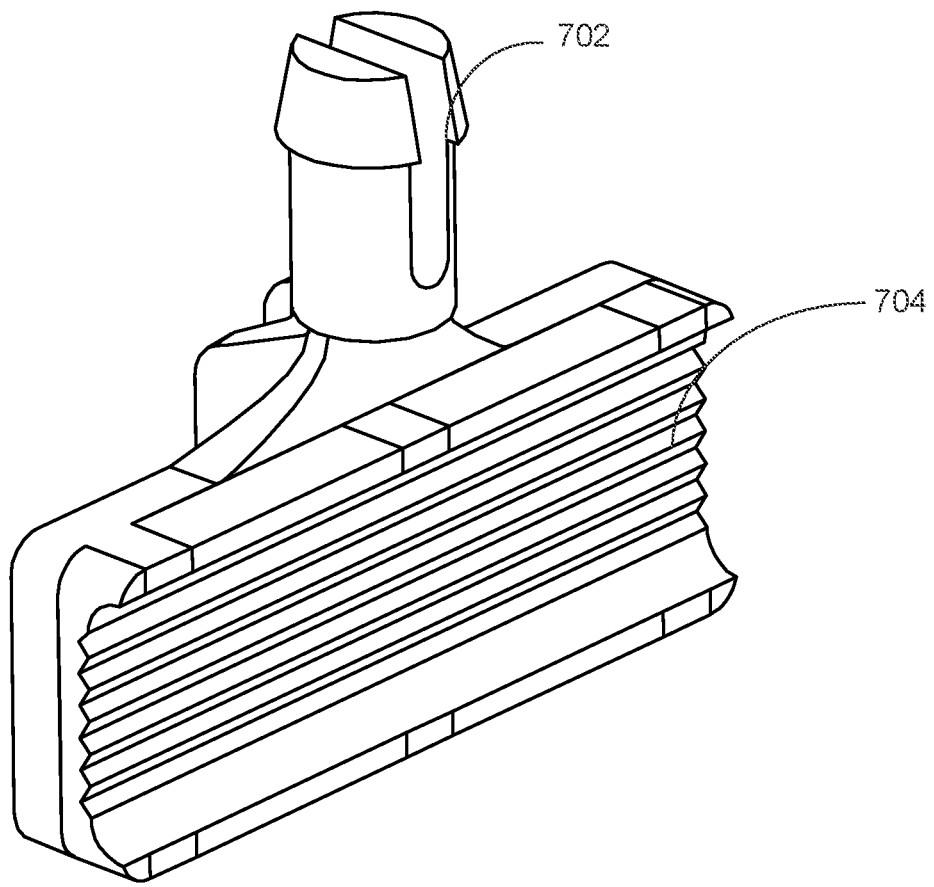
FIG. 7 is a perspective view of another exemplary blade according to another embodiment of the present disclosure.
Figure 8:
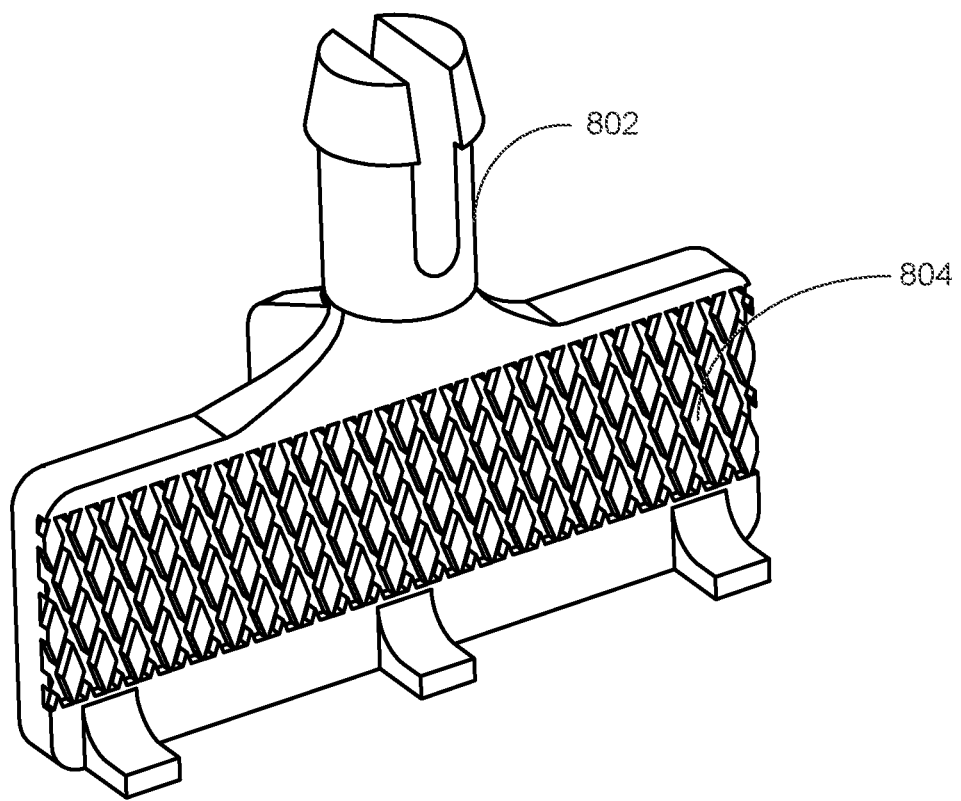
FIG. 8 is a perspective view of another exemplary blade according to another embodiment of the present disclosure.

Further adjustability can be provided by the replaceable or detachable blades as detailed in FIGS. 6-8. Depending upon the specific physiology of the patient, the surgeon may desire a blade that is either wider or narrower. Because the blades 602 can be removed and replaced, the surgeon can select a blade that fits the specific needs.

In some embodiments, the retraction device 102 includes a third frame portion (not shown) that may be detachably connected to the first frame portion 104. Moreover, should the particular use require an increased distance between the frame portions 104-106 and the blade 108A-108B, a post extension i.e. the third frame portion can be used to be inserted into the frame portions 104-106, to increase a length of the frame portions 104-106. When one or more clips of the first blade 108A (or 108B) are inserted into the post extension, the increased distance may be achieved.

The third frame portion may define a number of teeth that may extend along a length of the third frame portion. The teeth of the first frame portion 104 and the second frame portion 106 may align when the first frame portion 104 and the third frame portion are attached. Further, in some embodiments, the lever and gear mechanism 120 may be configured to engage the teeth of the first frame portion 104 and the third frame portion for moving the second frame portion along the first frame portion 104 and the third frame portion. An operator can extend the frame portions 104-106 using the third frame portions. Detachable third frame portions can be installed or removed based on the size of the opening that is needed for a particular surgery. The detachable third frame portions may allow surgeons to open up large spaces (up to 30 cm or more) when needed for some procedures. Otherwise, the surgeons can remove the third frame portion to perform procedures where the tissue opening needs to be smaller.

The third frame portion may be provided with two posts, which can be inserted into complimentary post recesses in the first and second frame portions 104-106. Further, a screw may be used to secure the third frame portions to the existing frame portions 104-106 by being inserted into a threaded recess in the frame portions 104-106. If an even further extension is desired, the third frame portion can be provided with additional post recesses (not shown) and the screw can have its own threaded recess (not shown), allowing for additional frame portions to be attached thereto, each with its own posts and screw(s). This assembly may permit functionally unlimited cavity sizes. This may be particularly useful when used in a veterinary setting, where the same retraction device can be used on animals of very different sizes, for example, both cats and horses.

Figure 1B:
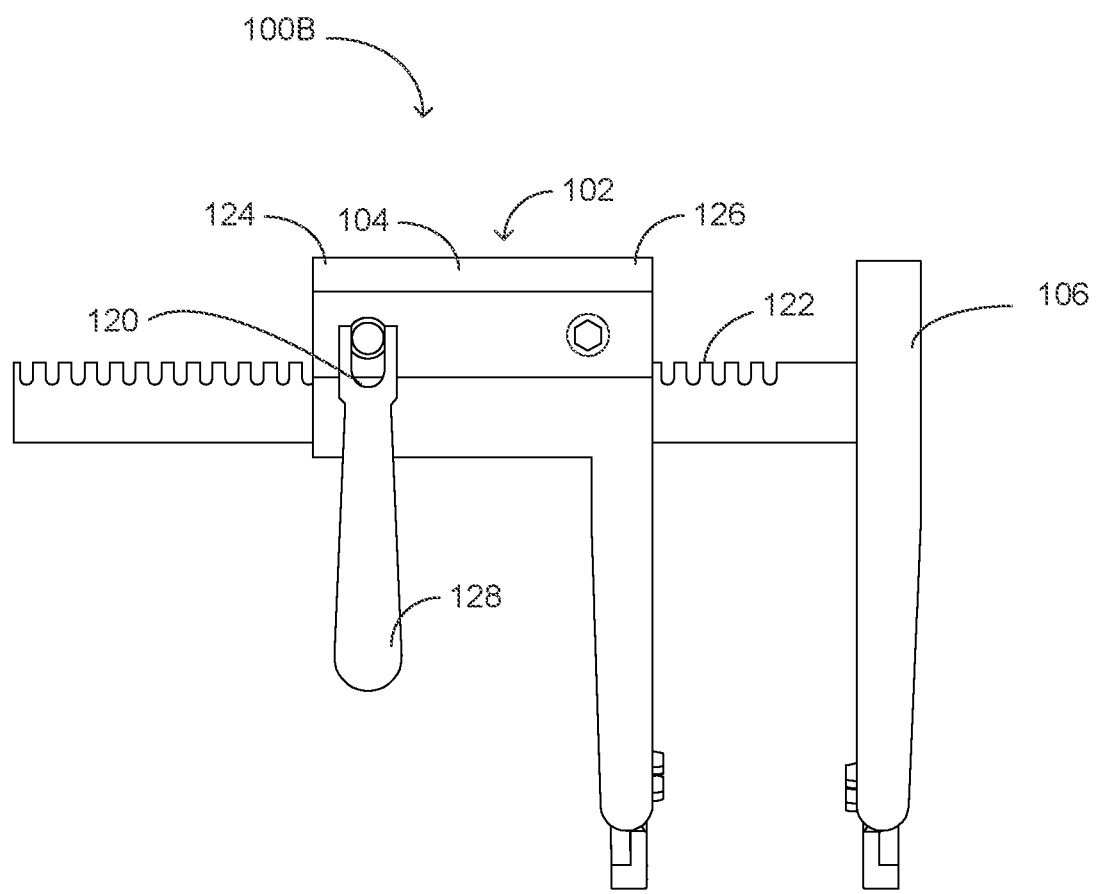
FIG. 1B is a schematic side view of the exemplary retraction device of FIG. 1 according to an embodiment of the present disclosure.

FIG. 1B is a schematic side view 100B of the exemplary retraction device 102 shown in FIG. 1A. FIG. 1B shows the second frame portion 106 in the second configuration. The lever and gear mechanism 120 may engage the teeth 122 of the first frame portion 104 for moving the second frame portion 106 from the first position to the second position. The retraction device 102 may also include a multiple drive system (not shown) operably engaged with the lever and gear mechanism 120. The multiple drive system may control the lever and the gear mechanism 120 in at least two different speeds for displacement rates per full rotation of the lever 120. In some embodiments, the lever and gear mechanism 120 further includes an operator-driven, moveable-gear element, connected to a worm gear element through a second movable gear element. Further, the lever and gear mechanism 120 may include a moveable, conical gear element, connected to a fixed conical gear element (not shown) through a belt (not shown). The multiple drive system may also include a handle 128 for moving the movable, conical gear element to adjust the position of the belt. Furthermore, the lever and gear mechanism 120 may include a second drive gear for the handle 128 configured to move the movable, conical gear element to adjust the position of the belt.

Figure 2A:
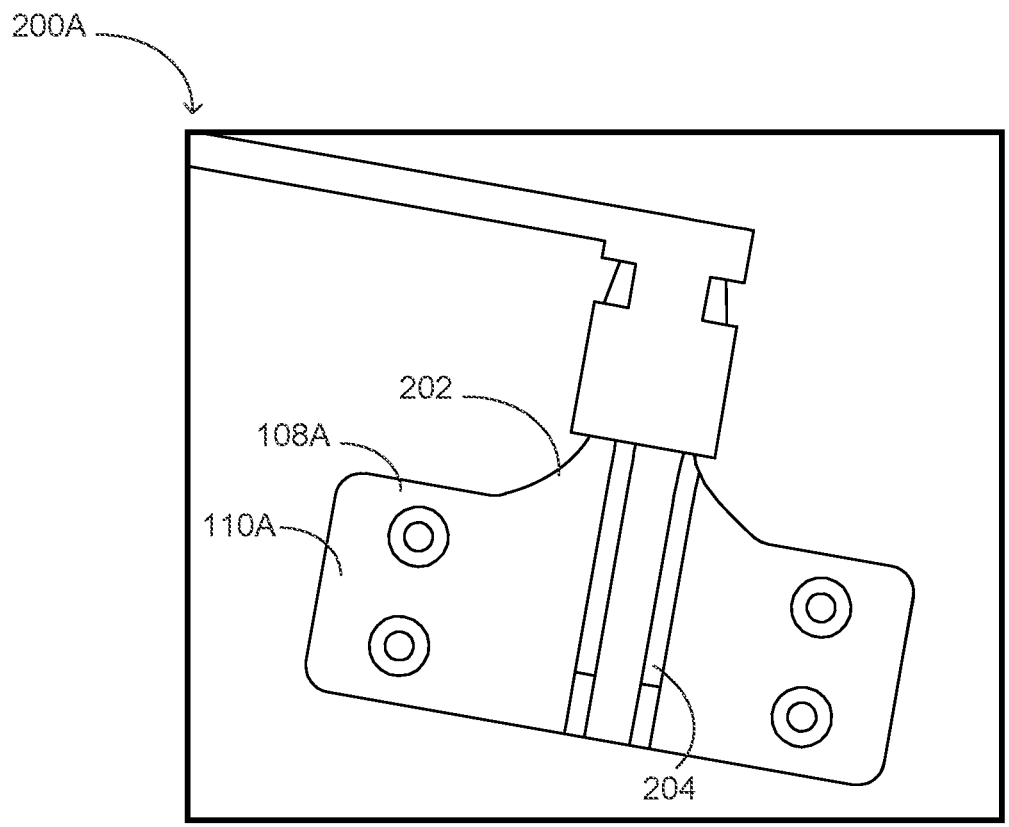
FIG. 2A is a schematic view of a portion of a first blade of the retraction device of FIGS. 1A-1B according to an embodiment of the present disclosure.

FIG. 2A is a schematic view of a portion 200A of the first blade 108A of the retraction device of FIGS. 1A-1B according to an embodiment of the present disclosure. As shown, the first blade 108A may include a flexible component 202. As discussed with reference to FIG. 1A, the flexible component 202 of the first blade 108A may be pivotally attached to the first frame portion 104. Further, as shown, the flexible component 202 of the first blade 108A may have the first surface 110A. The first surface 110A may include a locking structure 204 that may interlock with a locking structure of the second blade 108B. The locking structure 204 may be in the form of a pin or tab, which can be manually toggled or actuated to permit rotational movement. The locking structure 204 may be provided on one or both of the blades 108A-108B.

Figure 2B:
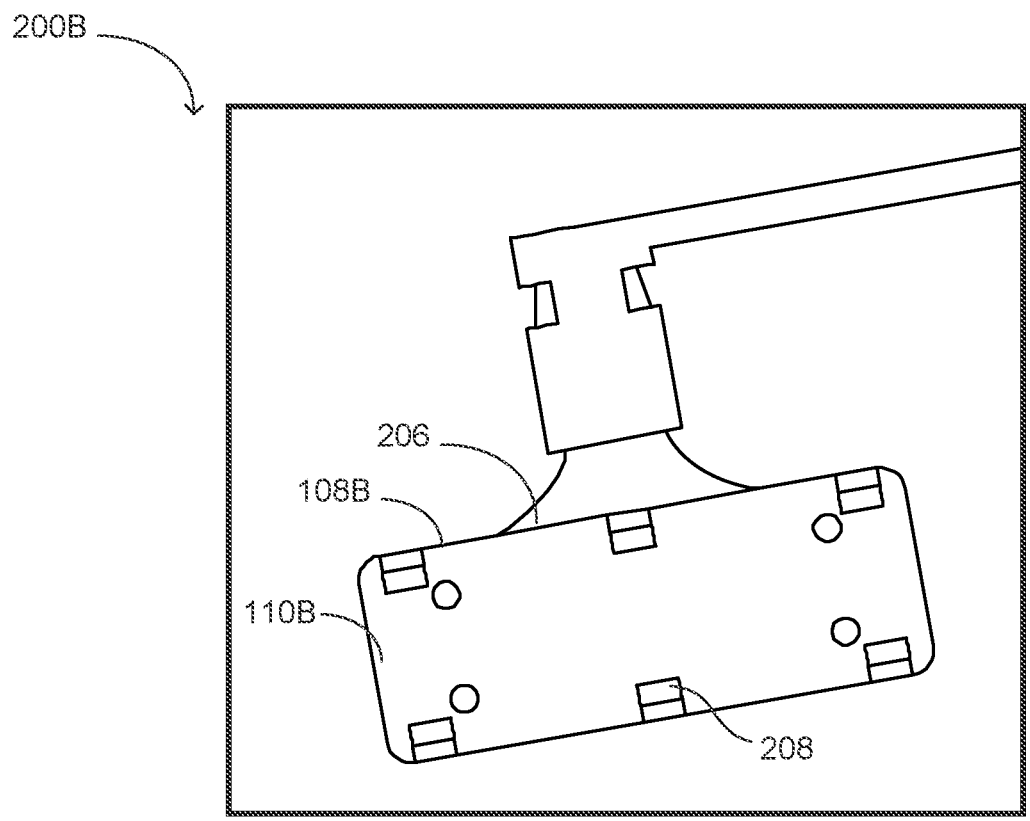
FIG. 2B is a schematic view of a portion of a second blade of the retraction device of FIGS. 1A-1B according to an embodiment of the present disclosure.

FIG. 2B is a schematic view of a portion 200B of the second blade 108B of the retraction device 102 of FIGS. 1A-1B according to an embodiment of the present disclosure. The second blade 108B may include a flexible component 206 pivotally attached to the second frame portion 106. The flexible component 206 of the second blade 108B may include the first surface 110B and the second surface 112B. The first surface 110B may substantially oppose the second surface 112B, respectively.

Turning now to FIG. 2B, the first surface 110A of the flexible component 202 of the first blade 108A may face the first surface 110B of the flexible component 206 of the second blade 108B. Further, the first surface 110B of the flexible component 206 may include a locking structure 208 in accordance with the locking structure 204 of the first blade 108A. The locking structures 208 and 204 may interlock with one another to prevent pivoting of the first blade 108A and the second blade 108B when the first surfaces 110A-110B are brought into proximity with one another.

Figure 3A:
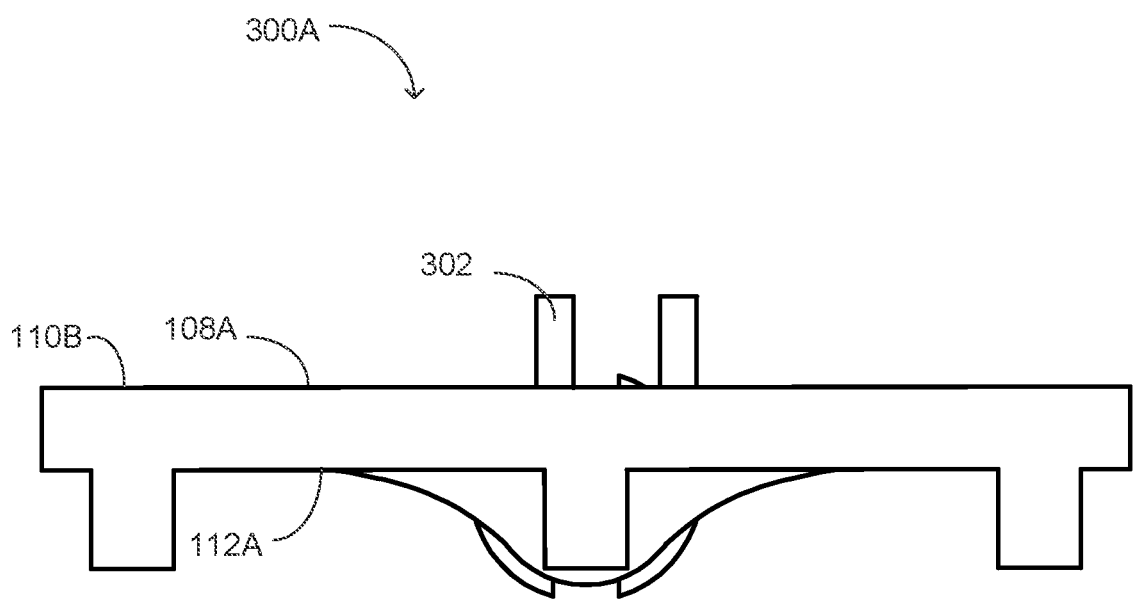
FIG. 3A is a schematic zoomed view of the first blade of the retraction device of FIGS. 1A-1B according to an embodiment of the present disclosure.

FIG. 3A is a schematic zoomed view 300A of the first blade 108A of the retraction device 102 of FIGS. 1A-1B according to an embodiment of the present disclosure. As shown, the first blade 108A includes the first surface 110A and the second surface 112A. The first surface 110A of the first blade 108A may include a locking structure 302.

Figure 3B:
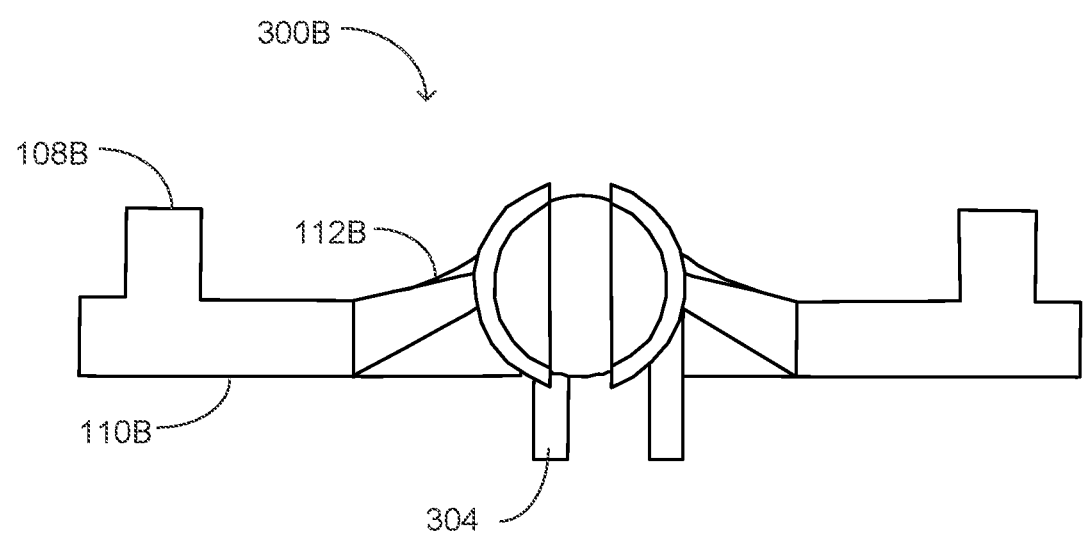
FIG. 3B is a schematic zoomed view of the second blade of the retraction device according to an embodiment of the present disclosure.

FIG. 3B is a schematic zoomed view 300B of the second blade 108B of the retraction device 102 of FIGS. 1A-1B according to an embodiment of the present disclosure. As shown, the second blade 108B includes the first surface 110B and the second surface 112B. The first surface 110B of the second blade 108B may include a locking structure 304.

Referring again to FIG. 3A, the locking structures 302 and 304 may interlock with one another to prevent pivoting of the first blade 108A and the second blade 108B when the first surfaces 110A-110B are brought into proximity with one another or contact one another.

Figure 4:
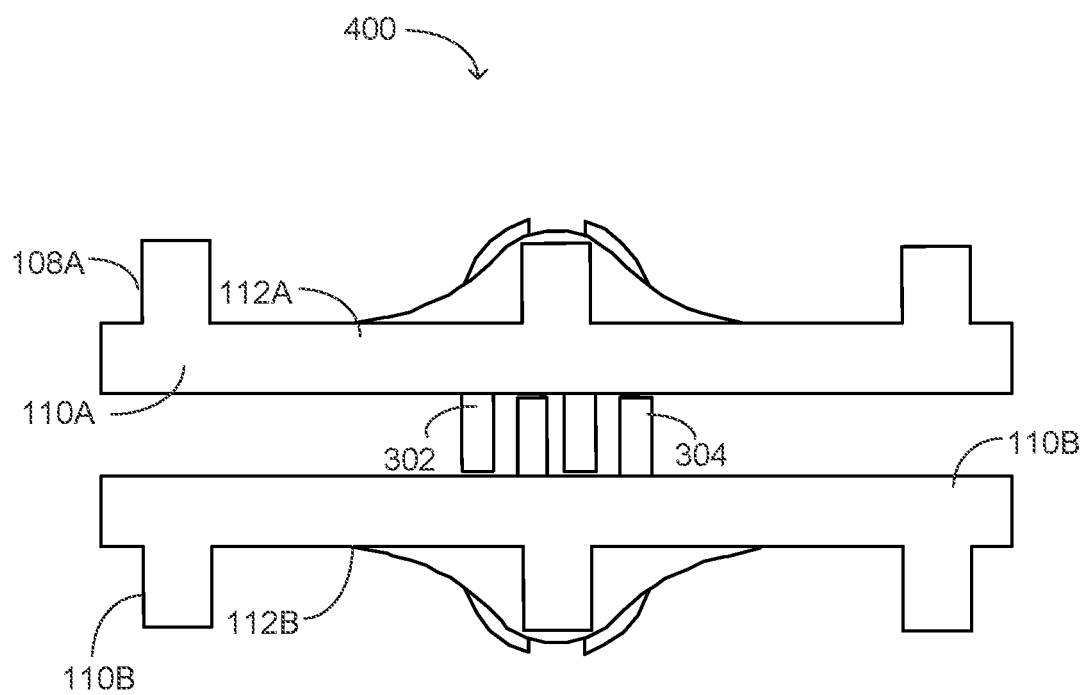
FIG. 4 is a schematic zoomed view of the first blade and the second blade of the retraction device in an interlocked configuration according to an embodiment of the present disclosure.

FIG. 4 is a schematic zoomed view 400 of the first blade 108A and the second blade 108B of the retraction device 102 in an interlocked configuration according to an embodiment of the present disclosure. As discussed with reference to FIGS. 3A-3B, the locking structure 302 of the first blade 108A and the locking structure 304 of the second blade 108B may interlock with each other to prevent pivoting of the first blade 108A and the second blade 108B when the first surfaces 110A-110B are brought into proximity with one another.

Figure 5A:
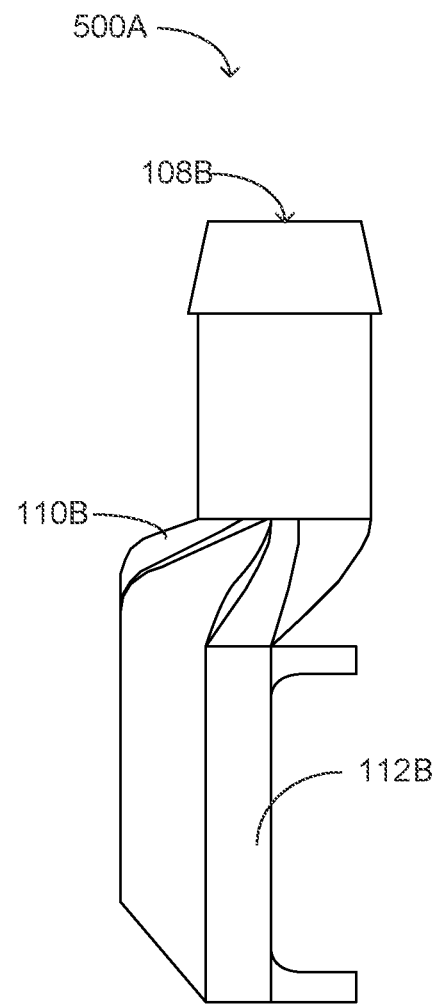
FIG. 5A is a schematic side view of the second blade according to an embodiment of the present disclosure.
Figure 5B:
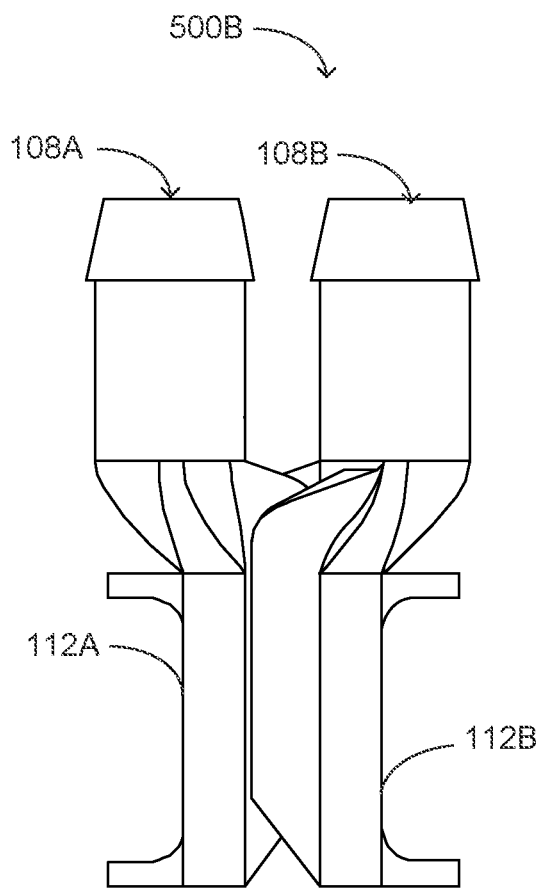
FIG. 5B is a schematic side view of the first blade and the second blade of the retraction device of FIGS. 1A-1B in the interlocked configuration according to an embodiment of the present disclosure.

FIG. 5A is a schematic side view 500A of the second frame portion 106 according to an embodiment of the present disclosure. FIG. 5B illustrates a schematic side view 500B of the first frame portion 104 and the second frame portion 106 of the retraction device 102 in the interlocked configuration according to an embodiment of the present disclosure.

FIG. 6 is a perspective view 600 of an exemplary blade 602 of a retraction device (for example, retraction device 102) according to an embodiment of the present disclosure. The blade 602 may be attached to a frame portion such as, the frame portion 104 as discussed with reference to FIG. 1A. The blade 602 is removable from the frame portion such as the frame portion 104. The blade 602 may include a first surface 604A and a second surface 604B opposing each other. The second surface 604B may come in direct contact with one or more tissues of a patient when an operator performs a surgery using the retraction device including the blade 602. The second surface 604B may include a padding material 608. The padding material 608 may include any suitable material such as silicon polymer, PDMS, and so forth. Further, the padding material 608 may have a constant modulus of elasticity between 0.5 Mega Pascal (MPa) and 15 MPa.

The padding material 608 may include a curved edge 606 for gripping tissue. The curved edge 606 may include including one or more rigids 610 segmented along a length of the edge 606 for gripping a tissue. The rigids 610 may allow flexure of the blade 602. The blade 602 may be formed using a sterilizable material. The padding material 608 can also have counter bored holes or T-slots 616 for the ridges 610.

The blade 602 may have a flat planar shape when not pressed against the ribs or tissues. Upon contact with the ribs/tissues, the blade 602 may take on a curved shape to adapt to the stiffness and unique shape of the patient's ribs/tissues. The padding material 608 may be chosen such that the modulus of elasticity with the area moment of inertia of the blade 602 matches the stiffness (EI) of the area being retracted.

In some embodiments, the blade 602 matches a radius of curvature of the tissue contacted during tissue displacement. In the case of a thoracic retractor, the blade 602 may match the radius of curvature of the patient's rib during retraction. One such example is shown in FIG. 6.

Since surgeons have different methods of separating the intercostal soft tissues during thoracotomy, it is possible that the blade 602 may come in contact with a composite of both soft (muscle) and hard tissues (ribs) during retraction. Therefore, different shape and size of the blade may be formed. FIG. 7 and FIG. 8 show two exemplary blades 702-802, respectively, having different cross sectional area.

When the blade (such as 602) has a flexural stiffness (N*m$^2$) that matches that of the tissues contacted, the radius of curvature of the blade and tissue can match and the blade 602 may apply a uniform load across the length of the tissue. The flexural stiffness of the blade 602 (or 702-802) may be determined by the product of the blade's cross sectional area moment of inertia (I) and the modulus of elasticity ($\varepsilon$). Intercostal tissue in humans has been found to have total flexural stiffness between 0.01 and 500 N*m$^2$. The blade's inducement of a bending moment on the tissue by application of a uniform, distributed load is important because it prevents the concentration of high stress (N/m$^2$) at discrete points on the tissue during retraction. The application of high stress points to human tissue by non-conforming tissue engaging devices is the primary cause of broken ribs and crushed intercostal vasculature and nerves during thoracotomy. This embodiment of the device designed to match the composite flexural stiffness of the tissues retracted provides the most uniform load possible and can minimize post-surgical pain for the patient while allowing an appropriate visual field for the surgeon.

In some embodiments, the padding material 608 is inert, non-toxic and non-flammable and may be classified as having no marked harmful effects on organisms in the environment (according to Ullmann's Encyclopedia of Industrial Chemistry), such as a silicone-based organic polymer, for example PDMS. The padding material 608 may form a layer or pad having a thickness of at least 0.5 mm, such as, between approximately 1 mm to 10 mm, between approximately 3 mm to 6 mm, and approximately 4 mm.

As discussed with reference to FIGS. 6-8, the blades 602-802 are removable and can be removed from the frame portions (such as frame portions 104-106). In some embodiments, the frame portions and the blades 602-802 are provided with connecting elements. For example, each frame portion can have a tube 612 extending outward, and transversely, into which clips (not shown) may be provided on the blades 602-802 are inserted. Connection of this particular prototype may be accomplished through a quick connect, allowing for easy removal and replacement of the blades 602-802. The tubes 612 may have a larger inner diameter proximal to the frame portions to allow the clips of the blades 602-802 to nest therein the retraction device 102.

The tubes 612 may also have openings 614 for compressing the barbed clips for easy insertion and removal. Alternatively, there may be a narrowing inside the tube 612 such that when the blade 602 (or 702-802) is rotated about the axis 45 to 90 degrees, the clips are compressed to allow for removal.

In alternative embodiments, for attachment the blade 602 includes a keyed connector that either can be rotated about the pivot to release the blade 602 or compressed. This may allow for the blade 602 to rotate after insertion to allow for more accurate force distribution, thereby reducing unnecessary injury to the patient. For example, as the blade 602 separate as the first frame portion (for example, frame portion 104) moves down the retraction device (102), i.e., away from the second frame portion 106, the forces exerted upon the blade 602 can similarly be parallel to the frame portions 104-106. Because the blades 602 of the frame portions 104-106 are permitted to rotate as they are separated, the retraction device 102 may allow the blades 602 to have significantly greater surface contact with the cavity within the patient's body. The increased surface contact area results in less force being exerted on any individual area, and therefore, less injury to patient tissues.

Turning now to FIG. 8, the blade 802 are provided with a number of teeth 804 configured to limit rotational movement of the blade 602 during insertion of the retraction device 102. The teeth 804 may be designed to mesh, such that forces tending to rotate the blade 802 can be hindered. The mesh teeth 804 may be configured to prevent the blade from sliding along the length of the ribs during rotational movement of the blade 602. In another embodiment, the blades 802 can be provided with a locking mechanism (not shown).

In some embodiments, for resisting, but not prohibiting rotational movement springs and structure holders (not shown) may be provided along with the tube 612, such that the blades 602 of the frame portions 104-106 are permitted to rotate, but only after overcoming a predetermined amount of force. Similarly, the blades 602 of the frame portions 104-106 may be maintained or biased to their not rotated condition by the holders. The amount of biasing force provided by the holders can be selected depending upon the specific uses. In other words, different retraction devices 102 can be selected (with different holders and different biasing forces) for treating different medical conditions.

Further, one or both of the blades 602 of the frame portions 104-106 may be provided with one or more tabs. The tabs may be designed to prevent the blades 602 from slipping out of the cavity with the blades 602 separate. In one embodiment, the tabs may extend perpendicularly from the blades 602 (or 108A-108B), but the angle defined by the blades 602 and the tabs can be at any angle, such as, at an angle larger than 45 degrees.

As discussed with reference to FIG. 7, the blade 702 can be reinforced along the axis of rotation with inter-digitated support to minimize deflection while the cross section is maintained along the length 704 of the rib to allow flexing.

As shown in FIG. 8, the use of inter-digitated support or the teeth 804 may allow the blade 802 to take on extremely thin thickness to fit in smallest possible incision space. The teeth 804 may help the blades 802 stay paired together in contact during installation. The blades 802 can be installed into the thoracic space without being attached to the frame portions 104-106. The interlocking mechanisms on the blades 802 may keep the blades 802 from sliding against each other and make it easier for the frame portions 104-106 to be attached to the blades 802. It is noted that a connector can support the bottom side of each of the blades 802 for controlling the amount of blade flexure. Additional connectors may be utilized to increase rigidity.

As discussed with reference to FIGS. 6-8, the blade 602 (or 702-802) may be reinforced along the axis of rotation to minimize deflection while the cross section is maintained along the length of the rib to allow flexing.

The blades 602 may have a very narrow insertion edge to reduce the space needed for insertion of the retraction device 102 into a cavity in the body. This can be achieved by having the edge 606 of the blades 602 distal the clips narrow, for example, tapered or stepped, such that the edge 606 has a significantly smaller cross section than other areas of the blade 602. In some embodiments, when the edges 606 of complimentary blades 602 are joined, as shown in FIG. 5B, the edges 606 may together form a very small narrow tip, necessarily reducing the size of the incision to be made by the doctor. Because the thickness of the blade 602 increases from the edge 606, inserting the blade 602 further into the cavity made by the incision can help to widen the incision without the doctor needing to cut further. In some embodiments, the padding material 608 may only present on a section of the blade 602, such that the tip formed by the two edges 606 of the blades 602 together is typically less than approximately 10 mm, preferably between approximately 2 mm and approximately 8 mm, and most preferably between approximately 3 mm and approximately 6 mm. The thickness of the blade 602 may be dependent upon the material (EI). Therefore, EI may be about 0.01 N*m$^2$ plus or minus an order of magnitude. The range may cover up to at least 500 N*m$^2$.

In some embodiments, the tubes 612 of each of the blades 602 are positioned on the frame portions 104-106 and the clips are positioned on the blades 602. In alternative embodiments, an annular cavity is disposed in the blade 602. A complimentary structure, e.g., barbed clips (not shown), could be used on the frame portions 104-106 to permit attachment of the blades 602 to the frame portions 104-106.

In some embodiments, the blade 602 may include a larger area for contacting the tissue. Accordingly, the padding material 608 may be provided on a larger section of the blade 602 as the surface contacting the tissue is also larger. In some embodiments, the padding material 608 is provided on the blade 602 only where the tissue is expected to contact the blade 602, and as a result, the padding material 608 is separated into two separate areas.

Further, the blade 602 may take on a variety of forms to accomplish the same goals as described above.

In an exemplary scenario for performing a surgery using the retraction device 102, a space of about 1 inch side is made in the sternum, pectoralis muscles, or ribs, before the blades are inserted. The total thickness of the lip formed by the blades in paired contact may be about 25.4 mm or less to fit the size of the incision. The total thickness may be about 10 mm-15 mm, but this may depend on the strength of the elastic properties of the material selected to make the blade. The tabs are positioned below the sternum with the padding material against the bone. When a ratcheting lever is actuated, the first frame portion is moved along the length of the retraction device 102. As a result, the first blade moves away from second blade, and the cavity is forced open. Each movement of the lever repeats this action until the cavity is open to the desired spacing.

As discussed with reference to FIG. 1, the frame portions 104-106 or other parts of the retraction device 102 may be manufactured from stainless steel or other autoclavable material with sufficient strength for retraction. The connection tubes (e.g. 612) may have a larger inner diameter proximal to the frame portions 104-106 to allow the clips of the blade to nest. The connection tubes also generally have two openings for compressing the barbed clips for removal (alternatively, there can be a narrowing inside the tube such that when the blade is rotated about the axis 45 to 90 degrees the clips are compressed to allow removal). Another option for attachment would be through a keyed connector that either needs to be rotated about the pivot to release blade or compressed. The reusable material may be such that it can withstand temperatures exceeding 115° C.

In some embodiments, the various components of the retraction device 102 are of a construction that allows for sterilization after a single use. This permits the retraction device 102 to be used multiple times without having to be replaced. However, in alternative embodiments, certain parts of the retraction device 102 may be designed to be replaced. This allow for a significantly broader class of materials to be used.

For example, many types of materials which are suitable to be used as the padding material on the blades, due to the correct physical properties, makes such materials incapable of withstanding the pressures and temperatures typically used in sterilization techniques. Therefore, in some embodiments, the connection between the blades and the remainder of the retraction device 102 is designed such that the blades (such as blades 108A-108B) can be removed. Accordingly, if the blades cannot be sterilized after use, it is possible to replace the blades with new blades, and the old blades removed and discarded. The replacement blades can be of different construction or of different materials than the blades that are removed. Thus, after an initial use, the blades would be removed and discarded awhile the remainder of the retractor would be sterilized by conventional methods. Thereafter, new blades would be connected.

Figure 9:
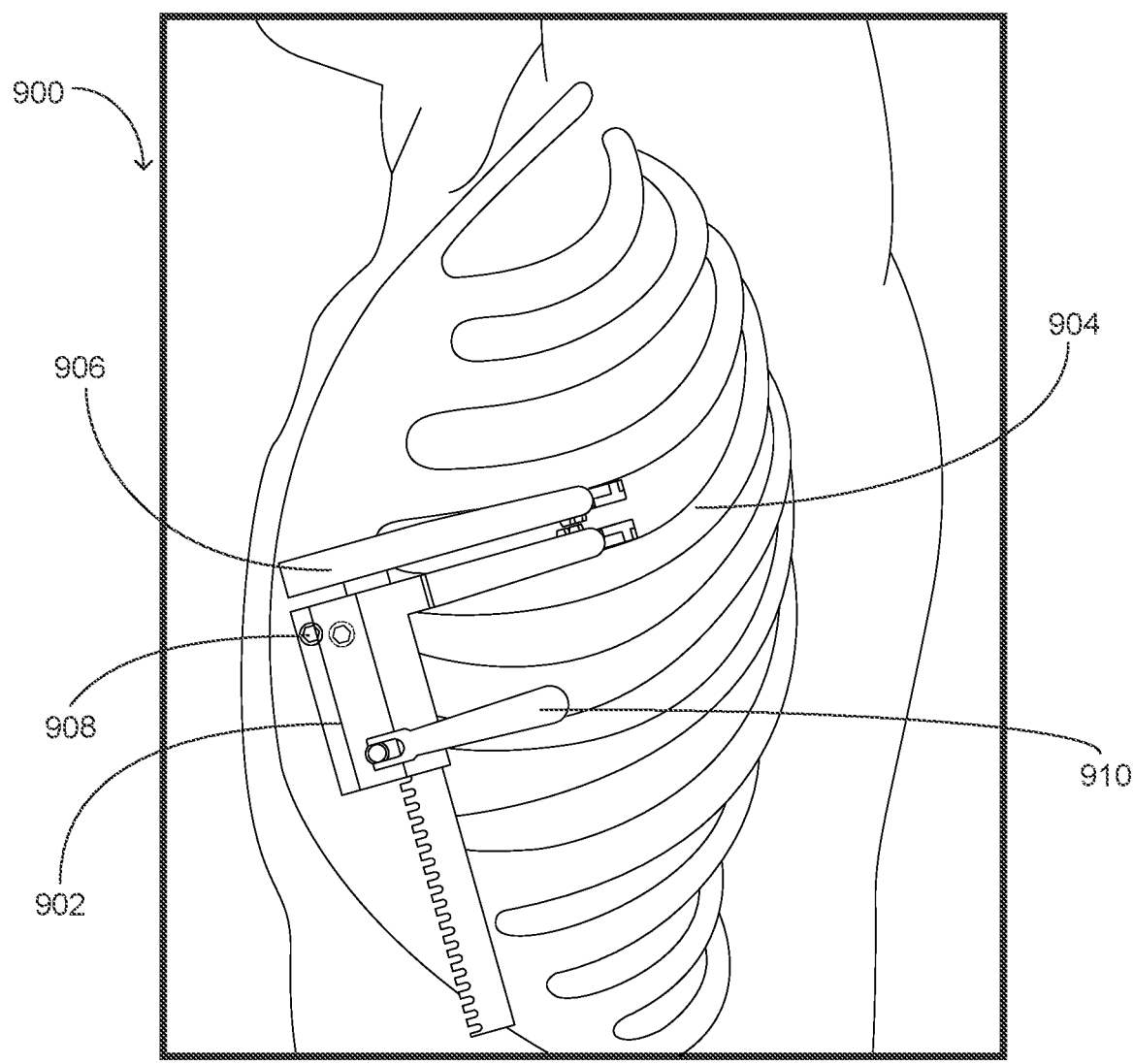
FIG. 9 is a schematic view illustrating a use of a retraction device for performing a medical procedure according to an embodiment of the present disclosure.

FIG. 9 is a schematic view 900 illustrating use of a retraction device 902 for performing a medical procedure according to an embodiment of the present disclosure. As shown, a first frame portion 906 and a second frame portion 908 may be inserted between in a cavity such that blades move between two ribs 904 of a patient. Thereafter, using a handle 910 of the retraction device 902, an operator may actuate the movement of the blades (not shown) for enlarging the cavity and performing the medical procedure. The blades may be manually rotated by the operator, or otherwise moved by the force applied by the ribs 904.

Figure 10:
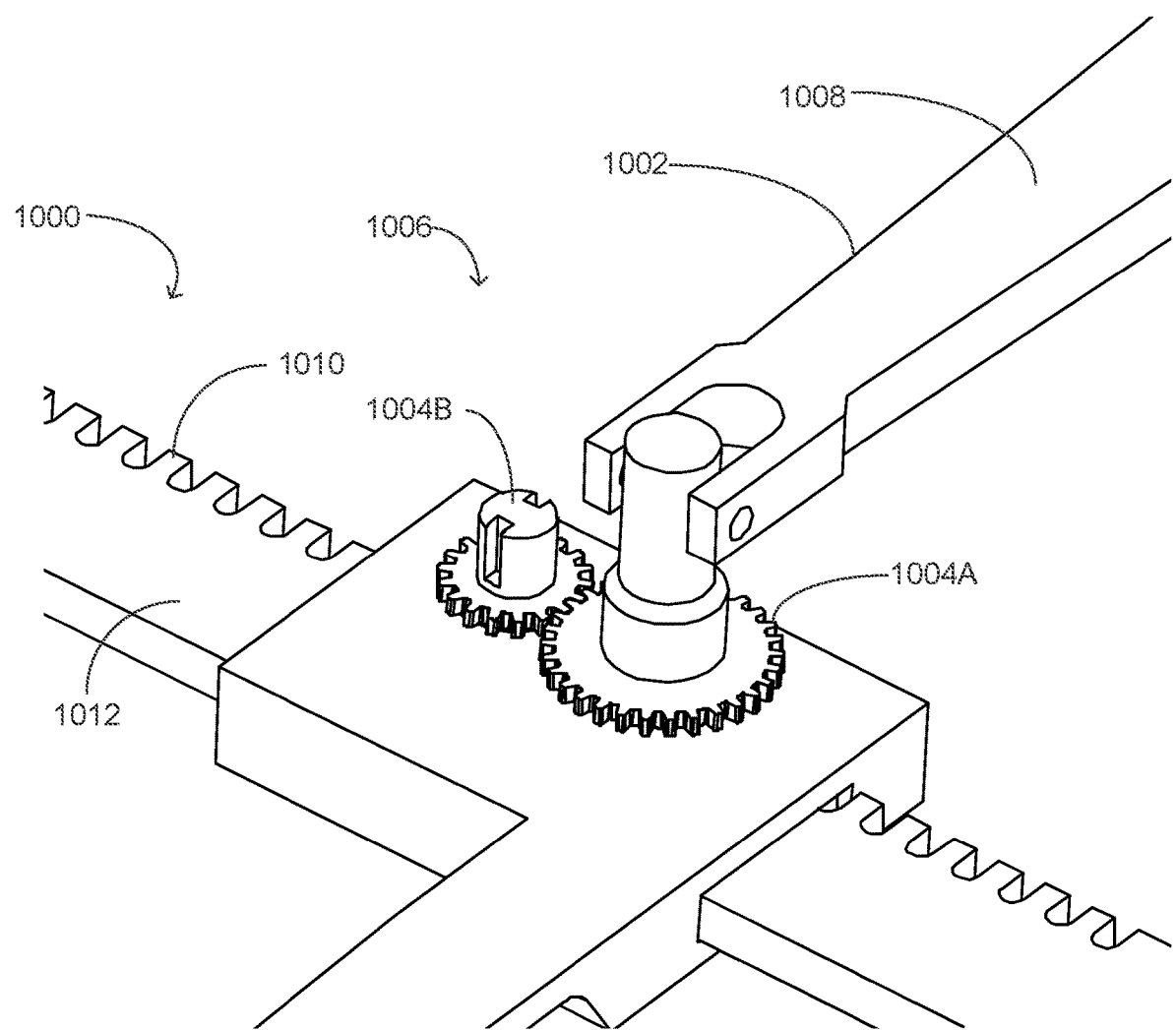
FIG. 10 is a perspective view of an exemplary lever and gear mechanism (or multiple drive opening mechanism) including at least two circular gears of a retraction device according to an embodiment of the present disclosure.

FIG. 10 is a perspective view 1000 of an exemplary lever and gear mechanism 1002 (or multiple drive opening mechanism) including at least two circular gears 1004A and 1004B of a retraction device 1006 according to an embodiment of the present disclosure. The retraction device 1006 may include a variable number of gears (circular gears 1004A-1004B) per unit length of the frame portions 104-106 to generate a more gradual opening of the chest per turn of the opening lever and gear mechanism 1002. This can be accomplished by having smaller gaps between the teeth of the frame portion of the retraction device 1006 as the first frame portion 104 moves along the length of the retraction device 102. The two circular gears 1004A and 1004B may be configured to drive a single rack and pinion mechanism.

Examples of the two circular gears 1004A and 1004B may include, but are not limited to, spur gears. The two circular gears 1004A and 1004B may rotate single internal pinion along teeth 1010 of a frame portion 1012 of the retraction device 1006. Further, only one of these two circular gears 1004A-1004B may remain in direct contact with the internal pinion. The internal pinion mechanism can be similar to the pinion mechanism implemented by other Finochietto style retractors known in the prior art. Additionally, the pinions size can be adjusted depending on the strength of the material that is used to make the pinion and the frame portion 1012. Additionally, the two circular gears 1004A and 1004B may have different diameters to allow for at least two different retraction speeds. The circular gears 1004A and 1004B may be in a 2:1 gear ratio so as to allow a normal speed and a half-speed retraction. Each of these circular gears 1004A and 1004B may have a protruding socket element that allows installation of the detachable handle 1008. Depending on the user's preference, the handle 1008 can be placed on either of the two circular wheels to select a retraction speed.

Further, the multiple gear mechanism 1002 may be configured to provide retraction speeds from 0 to 20 mm per handle rotation. Other example speeds are about 7.5 mm and about 15 mm per handle rotation. In this example, the handle 1008 is provided on the retraction device 1006 for allowing the surgeon to adjust down the rate at which the tissue is separated by pushing or pulling the handle and changing the diameter of the gear that moves down the frame portions of the retraction device 1006. This may also be accomplished by having a first conical gear structure, connected to a second conical gear structure by a fixed belt. When the handle 1008 may be pushed, the first conical gear structure slides on a shaft, thus changing the gear ratio through the belt to the second conical gear element. By increasing or decreasing the number of gears per unit length of the retractor frame or the gear ratio, the surgeon can slowly or quickly open up the thorax and avoid fracturing ribs.

Figure 11:
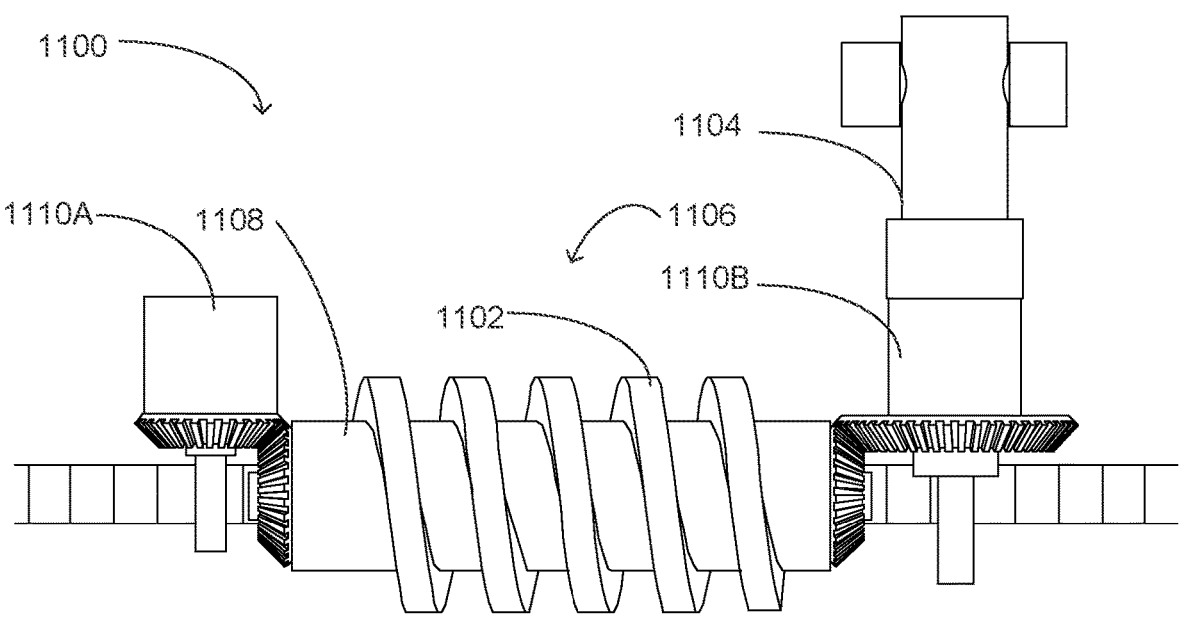
FIG. 11 is a zoomed cross-sectional view of an exemplary worm gear mechanism of an exemplary multiple drive opening mechanism of a retraction device according to an embodiment of the present disclosure.

FIG. 11 is a zoomed cross-sectional view 1100 of an exemplary worm gear mechanism 1102 of an exemplary multiple drive opening mechanism 1104 of a retraction device 1106 according to an embodiment of the present disclosure. The retraction device 1106 may include a fixed first frame portion and a movable second frame portion. In this embodiment of the opening mechanism, a single worm gear 1108 may be contained on or within a movable first frame portion movable second frame portion of the retraction device 1106. The first frame portion may define a number of teeth extending between a proximal end and a distal end of the first frame portion. The single worm gear 1108 may adjust the position of the movable second frame portion along the length of the first frame portion having teeth. The worm gear 1102 may be directly driving the displacement of the moveable second frame portion along the first frame portion having the teeth. The rotation of the worm gear 1102 may be driven by either of two miter or bevel gears 1110A and 1110B (also referred as worm driving gears) oriented at 90 degrees at both ends of the worm gear 1102. The first gear 1110A may drive the first end of the worm gear 1102 and may have a first diameter. The second gear 1110B may drive the second end of the worm gear 1102 and may have a second diameter. The driving of the worm gear 1102 with either of two diameter gears 1110A and 1110B may allow an operator to retract at two distinct speeds per full rotation of a handle (See 1008 of FIG. 10) of the gear mechanism 1104. The handle may be detachable and may be installed into one of the two worm driving gears 1110A and 1110B using a socket method.

According to some embodiments of the worm gear mechanism 1104, the two worm driving gears 1110A and 1110B of different diameters may be in contact with each other on one end of the worm gear mechanism 1104 containing a bevel or miter gear 1110A and 1110B at 90 degrees. This embodiment may reduce the number of gear elements on the worm gear mechanism 1104 by one. In this embodiment, the worm gear mechanism 1104 is driven on only one end and is in direct contact with only one of the driving gears 1110A and 1110B. The second worm driving gear 1110B may be in direct contact with the first worm driving gear 1110A, which is in contact with the worm gear 1110B. This design may allow selection between two different speeds of retraction per full rotation of the detachable handle mechanism.

Figure 12:
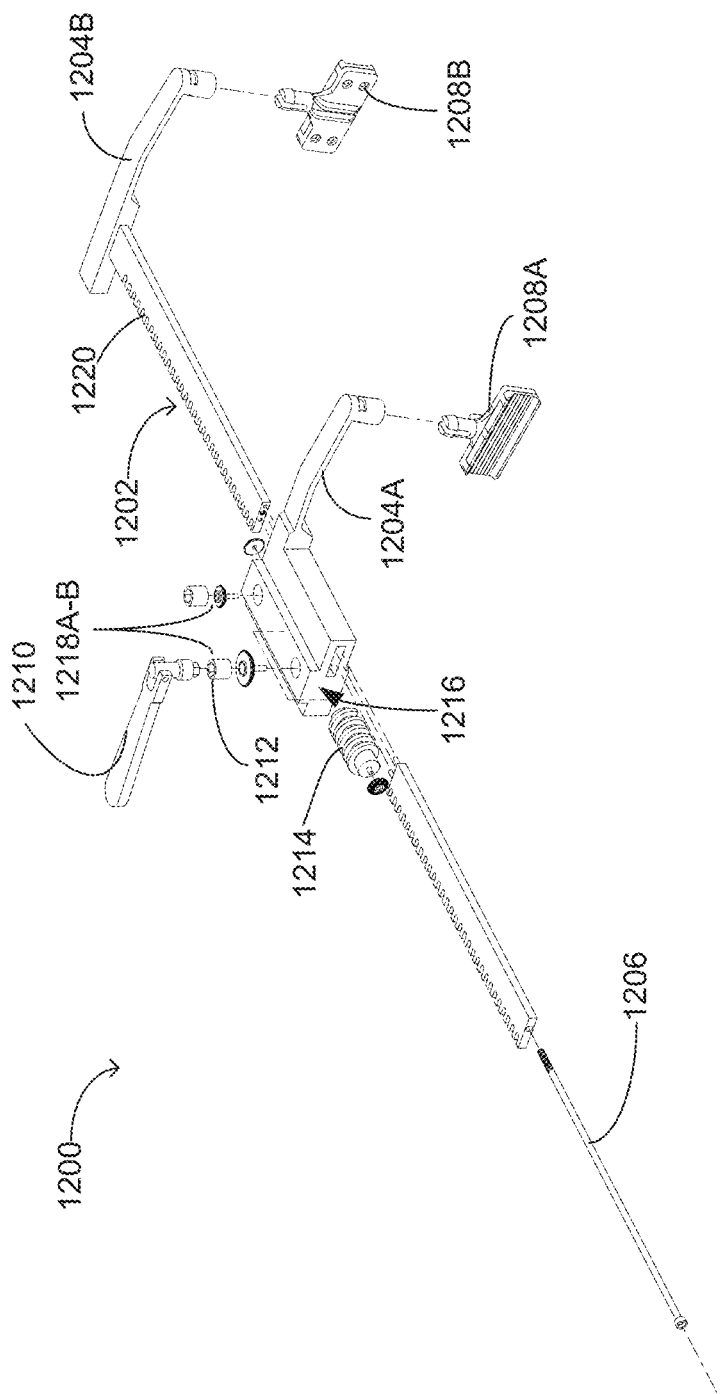
FIG. 12 is a perspective view of an exemplary retraction device containing a multiple drive worm gear mechanism and the retractor frame extension attachment (or a third frame portion) according to an embodiment of the present disclosure.

FIG. 12 is a perspective view 1200 of an exemplary retraction device 1202 containing a multiple drive worm gear mechanism 1212 and the retractor frame extension attachment 1206 (or a third frame portion) according to an embodiment of the present disclosure. The retraction device 1202 may include a first frame portion 1204A, and a second frame portion 1204B. Flexible blades 1208A and 1208B may be installed by an operator and may be secured by a connection mechanism that can allow the blades 1208A and 1208B to freely rotate when the opposing flexible blades 1208A and 1208B are not in contact with one another.

Further, the retraction device 1202 may include the multiple worm gear mechanism 1212 that may be actuated by the operator using a handle 1210 of the multiple worm gear mechanism 1212. The multiple worm gear mechanism 1212 may include multiple worm gear 1214 capable of being shielded and encased within a hollow internal portion or body 1216 of the first frame portion 1204A. Further, two gears 1218A and 1218B that drive the single worm gear 1214 may also be encased within the hollow portion 1216. The encasement of the gears 1218A and 1218B (and 1214) may help to prevent entrapment of patient tissue and surgical tools in teeth 1220 of the first frame portion 1204A. The frame extension attachment or the third frame portion 1206 may allow an opening size to be increased beyond the length of the standard frame portions (i.e. 1204A and 104B). The third frame portion 1206 may include one or more male pins or prongs that may insert into female sockets on the end of the first or second frame portions 1204A and 1204B of the retraction device 1202. The purpose of the prong socket mechanism is to align the two connected frames so that the movable second frame portion 1204B can move between the first frame portion 1204A and the third frame portion 1206 seamlessly. Once the third frame portion 1206 has been connected using the socket mechanism, the frame portions 1206 and 1204A or 1204B may be secured together using a threaded bolt that runs through the center of the third frame portion 1206 and may screw into a threaded hole in the center of the end of the original retractor frame i.e. frame portions 1204A and 1204B. The unthread end of the bolt may have a socket to allow a hand tool to be installed. The operator may subsequently turn the non-thread end of the bolt, causing the two frame portions (1206 and 1204A or 1204 B) to tighten and secure together. The operator may turn the bolt in the opposite direction to release the third frame portion.

An initial comparative study or experiment was performed in a pig cadaver model that characterized the force distribution profiles of two different retractor blades during surgery. The flat blades of a stainless steel Finochietto retractor were compared to a prototyped blade 108A-B of the invention embodiment depicted in FIG. 3. The prototyped blade 108A-B was constructed of ABSplus thermoplastic (layer thickness 0.254 mm) that was 3D printed using a Stratasys uPrint SE Plus. The prototyped blade 108A-B had total ABSplus thickness of 4 mm. A 2×5 array of single element force sensors was placed directly on the tissue engaging face of blade 108A-B. The five pairs of force sensors were arranged to measure the average pressure over five equally spaced segments along the length of the tissue engaging face of blades 108A-B. Both types of blades had tissue engaging faces with dimensions 66 mm×25 mm.

The force sensors were connected to a custom analog signal amplification circuit which was connected to computer controlled data acquisition unit. A mechanical plate with pistons was placed on top of each force sensor pair to ensure complete transfer of force to the sensing areas of the force sensors. Then a custom molded 3 mm silicone pad (as shown in FIG. 3) was placed on top of the five mechanical loading plates of the prototyped blades 108A-B. The Finochietto retractor blades had identical force measuring setups installed, however no silicone pad was placed on top of the mechanical loading plates. The Finochietto retractor had metal in direct contact with the pig tissue.

Three pig cadavers weighing between 154-176 kg had lateral thoracotomies performed on both sides using the instrumented Finochietto and prototyped retractors. The lateral incision lengths were all 20.0 cm in length. All retractions on these pigs were performed until the tissue opening was 40.00 mm in height. The retraction forces recorded by the force sensor arrays for both retractors were compared when the retraction reached 40.00 mm. All retraction forces are expressed in units of Newtons (N).

Figure 13:
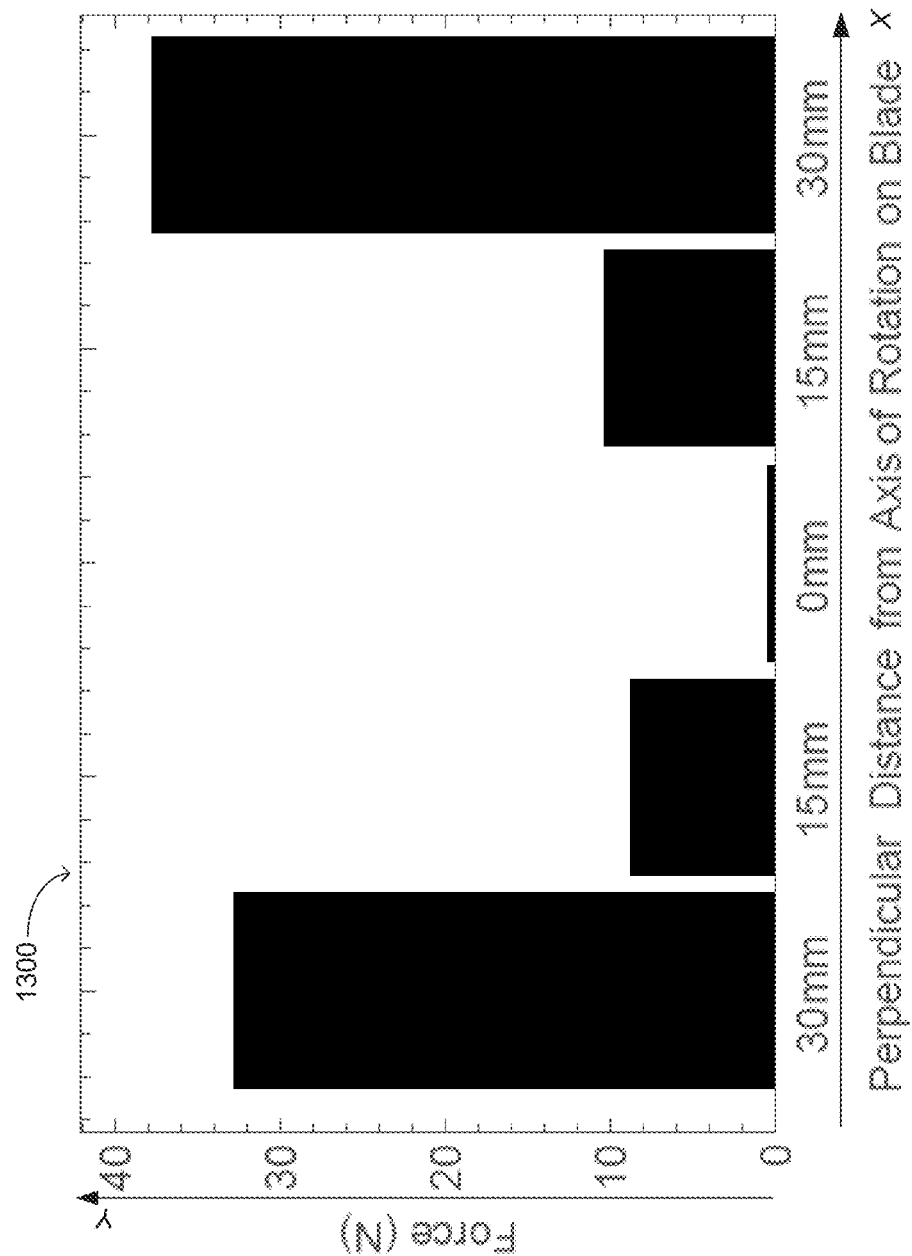
FIG. 13 is a graph depicting the distribution of retraction forces collected along a pig's rib using the recording instrumentation previously described at a 40.00 mm thoracotomy retraction distance using the Finochietto retractor.

FIG. 13 is a graph depicting the distribution of retraction forces collected along a pig's rib using the recording instrumentation previously described at a 40.00 mm thoracotomy retraction distance using the Finochietto retractor. Each bar represents the force measured by a sensor pair at a perpendicular distance (millimeters) from the rotational axis of the blades. Herein, the term rotational axis may be used to describe the central axis of both retractor blades 108A-108B, however the blades of the Finochietto retractor were not permitted to rotate. The prototyped blades 108A-108B may be permitted to rotate. The two measurements taken 30 mm from the rotational axis represent the forces applied by the retractor blade at its two distal ends. The data from a single trial in FIG. 13 indicates that the distal ends of the Finochietto blade applied noticeably higher levels of force compared to the other blade locations during the trial. In this trial the center (0 mm in FIG. 13) of the Finochietto blade did not maintain contact with the ribs at the 40.00 mm retraction distance as the rib bent around a fixed-shape, metal retractor blade. The results of this type of force distribution for the retractor blade can cause significant damage to the tissues; including rib fracture.

Figure 14:
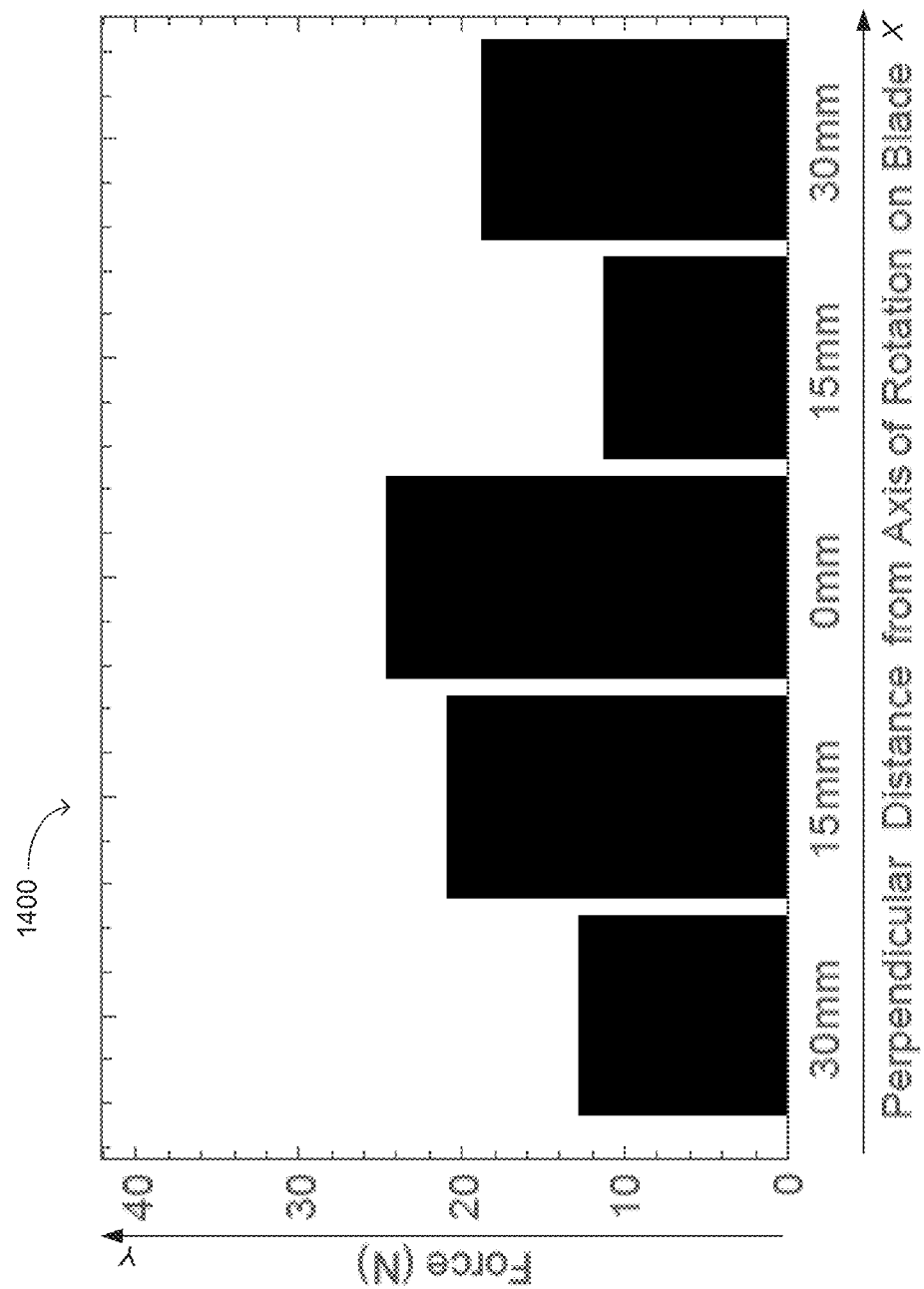
FIG. 14 shows the retraction force distribution during a thoracotomy performed on a pig with the prototyped retractor blade, such as blades according to an embodiment of the present disclosure.

FIG. 14 shows the retraction force distribution during a thoracotomy performed on a pig with the prototyped retractor blade, such as blades 108A and 108B. Compared to the Finochietto, the blades 108A-108B may apply a more uniform distribution of retraction force along the length of the blade (distances 30, 15, 0, 15, 30 mm in Fig. B). The blades 108A and 108B may have a flexible structure that allowed it to maintain contact with the ribs along the blade's lateral length. The maximum force applied by each of the blades 108A and 1008B at any single location is 25 Newtons compared to the over-30 Newton measurements seen on the distal ends of the Finochietto blade. The total force across all sensor pairs in these two retractor type trials FIGS. 13 and 14 were approximately 85 Newtons at the same retraction distance (40.00 mm). However, their force distribution profiles were noticeably dissimilar. The use of a flexible retractor blades 108A and 108B may prevent unnecessary tissue damage to a patient's tissue during surgery.

An embodiment of the present disclosure provides a method for preventing damage of one or more tissues within a body of a patient while performing a medical procedure by an operator. The method includes selecting a pair of blades, and attaching the selected blades to the disclosed retraction device (such as the retraction device 102). The method also includes aligning the blades parallel to each other by interlocking the blades along the complimentary mating surfaces of the blades. The method further includes inserting the blades into a cavity in a patient's body. The method further includes separating the blades to enlarge the cavity. The method further includes rotating the blades.

According to an aspect of the present disclosure the retraction device may be designed to engage patient tissue with a flexible material that may minimize maximum forces exerted on the patients' tissues and bones by increasing the contact surface area between the retractor blades and tissue, independent of the patient's unique anatomical intercostal features. The minimization of local stresses applied to the patient's tissues during thoracic retraction in turn may reduce surgical damage to the patient's intercostal and inter-sternal tissue.

Reference throughout this specification to "a select embodiment", "one embodiment", or "an embodiment" means that a particular feature, structure, or characteristic described in connection with the embodiment is included in at least one embodiment of the disclosed subject matter. Thus, appearances of the phrases "a select embodiment", "in one embodiment", or "in an embodiment" in various places throughout this specification are not necessarily referring to the same embodiment.

Furthermore, the described features, structures, or characteristics may be combined in any suitable manner in one or more embodiments. In the following description, numerous specific details are provided, to provide a thorough understanding of embodiments of the disclosed subject matter. One skilled in the relevant art will recognize, however, that the disclosed subject matter can be practiced without one or more of the specific details, or with other methods, components, materials, etc. In other instances, well-known structures, materials, or operations are not shown or described in detail to avoid obscuring aspects of the disclosed subject matter.

The above specification, examples and data provide a complete description of the structure and use of exemplary embodiments of the present disclosure. Although various embodiments of the present disclosure have been described above with a certain degree of particularity, or with reference to one or more individual embodiments, those skilled in the art could make numerous alterations to the disclosed embodiments without departing from the spirit or scope of this present disclosure. In particular, it should be understood that the described technology may be employed independent of a personal computer. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the present disclosure as defined in the following claims.

It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art, which are also intended to be encompassed by the following claims.

The above description does not provide specific details of manufacture or design of the various components. Those of skill in the art are familiar with such details, and unless departures from those techniques are set out, techniques, known, related art or later developed designs and materials should be employed. Those in the art are capable of choosing suitable manufacturing and design details.

The terminology used herein is for the purpose of describing particular embodiments only and is not intended to be limiting of the disclosure. It will be appreciated that several of the above-disclosed and other features and functions, or alternatives thereof, may be combined into other systems, methods, or applications. Various presently unforeseen or unanticipated alternatives, modifications, variations, or improvements therein may subsequently be made by those skilled in the art without departing from the scope of the present disclosure as encompassed by the following claims.

Features from one embodiment or aspect may be combined with features from any other embodiment or aspect in any appropriate combination. For example, any individual or collective features of method aspects or embodiments may be applied to apparatus, system, product, or component aspects of embodiments and vice versa.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed:

1. A retraction device comprising:
   a first frame portion including a proximal end and a distal end, and wherein the first frame portion defines a plurality of teeth extending between the proximal end and the distal end;
   a second frame portion being attached to and mechanically movable between a first position and a second position with respect to the first frame portion;
   a first blade being attached to the first frame portion and comprising a flexible material;
   a second blade being attached to the second frame portion and comprising a flexible material;
   a lever and gear mechanism attached to the second frame portion and configured to engage the teeth for moving the second frame portion between the first position and the second position; and
   a multiple drive system operably engaged with the lever and gear mechanism and configured to control the lever and gear mechanism in at least two different speeds for displacement rates per full rotation of the lever.

2. The retraction device of claim 1, wherein the lever and gear mechanism further comprises an operator-driven, moveable-gear element, connected to a worm gear element through a second movable gear element.

3. The retraction device of claim 2, wherein the first blade and the second blade are configured to apply spreading forces between 0 and 300 pounds.

4. The retraction device of claim 2, wherein the lever and gear mechanism comprises multiple components configured to be disassembled for cleaning and sterilization.

5. The retraction device of claim 2, further comprises a handle, and wherein the lever and gear mechanism further comprises a second drive gear for the handle configured to move the movable, gear element to adjust the position of the second frame.

6. The retraction device of claim 5, wherein the first blade and the second blade are configured to apply spreading forces between 0 and 300 pounds.

7. The retraction device of claim 5, wherein the lever and gear mechanism comprises multiple components configured to be disassembled for cleaning and sterilization.

8. The retraction device of claim 1, wherein the lever and gear mechanism further comprises a moveable, conical gear element, connected to a fixed conical gear element through a belt.

9. The retraction device of claim 8, wherein the first blade and the second blade are configured to apply spreading forces between 0 and 300 pounds.

10. The retraction device of claim 8, wherein the lever and gear mechanism comprises multiple components configured to be disassembled for cleaning and sterilization.

11. The retraction device of claim 8, wherein the multiple drive system further comprises a handle configured to move the movable, conical gear element to adjust the position of the belt.

12. The retraction device of claim 1, wherein the drive assembly further comprises a removable handle.

13. The retraction device of claim 1, wherein the first frame and the second frame are made of a sterilizable material.

* * * * *